US012755476B2

(12) United States Patent
Dam Hieu et al.

(10) Patent No.: US 12,755,476 B2
(45) Date of Patent: Oct. 6, 2026

(54) 3D ENHANCED VISUALIZATION OF MEDICAL IMAGES

(71) Applicant: GE Precision Healthcare LLC, Waukesha, WI (US)

(72) Inventors: Caroline Dam Hieu, Paris (FR); Pierrick Chevaillier, Antony (FR); Charly Girot, Paris (FR); Nicolas Gogin, Buc (FR)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 181 days.

(21) Appl. No.: 18/612,901

(22) Filed: Mar. 21, 2024

(65) Prior Publication Data

US 2025/0299422 A1 Sep. 25, 2025

(51) Int. Cl.

| | |
|---|---|
| ***G06T 15/08*** | (2011.01) |
| ***A61B 6/00*** | (2006.01) |
| ***A61B 6/46*** | (2024.01) |
| ***G06T 7/00*** | (2017.01) |
| ***G06T 7/11*** | (2017.01) |
| ***G06T 15/04*** | (2011.01) |

(Continued)

(52) U.S. Cl.

CPC .............. *G06T 15/08* (2013.01); *A61B 6/466* (2013.01); *A61B 6/5217* (2013.01); *G06T 7/0012* (2013.01); *G06T 7/11* (2017.01); *G06T 15/04* (2013.01); *G16H 30/40* (2018.01); *G16H 70/60* (2018.01); *G06T 2207/10081* (2013.01); *G06T 2207/30004* (2013.01); *G06T 2210/41* (2013.01); *G06T 2210/62* (2013.01)

(58) Field of Classification Search

None

See application file for complete search history.

(56) References Cited

U.S. PATENT DOCUMENTS

| | | | |
|---|---|---|---|
| 7,532,214 | B2 | 5/2009 | Lundström |
| 11,094,138 | B2 | 8/2021 | Canfield et al. |
| 2012/0249546 | A1 | 10/2012 | Tschirren et al. |

(Continued)

OTHER PUBLICATIONS

Courot et al., "Automatic cervical lymphadenopathy segmentation from CT data using deep learning", Diagnostic and Interventional Imaging, vol. 102, No. 11, Nov. 1, 2021 (Nov. 1, 2021), pp. 675-681, XP093280335, ISSN: 2211-5684, DOI: 10.1016/j.diii.2021.04.009, 8 pages.

(Continued)

*Primary Examiner* — Yanna Wu

(74) *Attorney, Agent, or Firm* — McCoy Russell LLP

(57) ABSTRACT

Methods and systems are provided for generating an enhanced 3D visualization of pathologies detected in a medical imaging examination. In accordance with one method, one or more AI algorithms may be applied to an image volume to detect a pathology in the anatomy, and prior to rendering the image volume for display, information about the pathology may be extracted from findings of the one or more AI algorithms, and different, customized rendering parameters may be calculated for the pathology and for each organ and/or system of a plurality of organs and/or systems surrounding the pathology, based on the extracted information. The image volume may then be rendered on a display device based on the customized rendering parameters.

17 Claims, 16 Drawing Sheets
(11 of 16 Drawing Sheet(s) Filed in Color)

(51) Int. Cl.
*G16H 30/40* (2018.01)
*G16H 70/60* (2018.01)

(56) References Cited

U.S. PATENT DOCUMENTS

| | | | | |
|---|---|---|---|---|
| 2019/0213778 | A1* | 7/2019 | Du | G06T 15/04 |
| 2025/0014690 | A1* | 1/2025 | Jacobs | G06T 17/00 |
| 2025/0213226 | A1* | 7/2025 | Sutton | A61B 6/501 |

OTHER PUBLICATIONS

International Application No. PCT/US2025/020727 filed on Mar. 20, 2025, International Search Report and Written Opinion issued Jun. 13, 2025, 17 pages.

Soni et al., "Convolutional neural network based CT scan classification method for COVID-19 test validation", Smart Health, vol. 25, Sep. 1, 2022 (Sep. 1, 2022), p. 100296, XP093280421, ISSN: 2352-6483, DOI: 10.1016/j.smhl.2022.100296, 12 pages.

Viola et al., "Importance-Driven Focus of Attention", IEEE Transactions on Visualization and Computer Graphics, vol. 12, No. 5, Sep. 1, 2006 (Sep. 1, 2006), pp. 933-940, XP093280336, USA ISSN: 1077-2626, DOI: 10.1109/TVCG.2006.152, 8 pages.

* cited by examiner

3D ENHANCED VISUALIZATION OF MEDICAL IMAGES

TECHNICAL FIELD

Embodiments of the subject matter disclosed herein relate to medical images, and in particular, to visualizing findings generated by AI algorithms.

BACKGROUND

In X-ray based imaging systems, such as computed tomography (CT) imaging systems, an electron beam generated by a cathode is directed towards a target within an X-ray tube. A fan-shaped or cone-shaped beam of X-rays produced by electrons colliding with the target is directed towards an object, such as an anatomy of a patient. After being attenuated by the object, the X-rays impinge upon an array of radiation detectors. Projection data acquired at the radiation detectors may be used to reconstruct an image volume of the anatomy.

One or more artificial intelligence (AI) algorithms may be used to segment regions in the image volume, such as organs or bones, and/or to detect pathologies in the image volume, such as tumors, lesions, nodules, etc. However, rendering parameters for displaying the image volume may not be optimized to visualize the pathologies effectively. For example, a tumor may be displayed as a solid object within the image volume, and various organs and bones around the tumor may be displayed with a degree of transparency that allows the tumor to be seen. However, the degree of transparency may be similar for the various organs and bones, causing visual distractions that may cloud a view of the tumor. Additionally, a suitable viewing angle of the image volume that shows features of the tumor clearly may be determined in a cumbersome, trial and error fashion.

SUMMARY

The current disclosure at least partially addresses one or more of the above identified issues by a method for an image processing system, the method comprising receiving an image volume of an anatomy of a patient; performing a segmentation of anatomies of the image volume; applying one or more artificial intelligence (AI) algorithms to the segmented image volume to detect a pathology in the anatomy; and prior to rendering the image volume for display, extracting information about the pathology from findings of the one or more AI algorithms; calculating different, customized rendering parameters for the pathology findings, and for each organ and/or system of a plurality of organs and/or systems surrounding the pathology, based on the extracted information; and rendering the image volume on a display device, based on the customized rendering parameters.

The issues may also be addressed by an image processing system comprising a processor and a memory including instructions that when executed, cause the processor to receive an image volume of a patient from a medical imaging system; detect a pathology in the image volume using an artificial intelligence (AI) algorithm; and prior to rendering the image volume for display, extract clinical information about the pathology from an output of the AI algorithm; and calculate customized rendering parameters for each of the pathology and each organ and/or system of a plurality of organs and/or systems surrounding the pathology, based on the extracted clinical information; and render the image volume on a display device, based on the customized rendering parameters. Specifically, a method for visualizing findings of one or more artificial intelligence (AI) algorithms trained to detect a pathology in an image volume of an anatomy of a patient may comprise extracting clinical information about the pathology from the findings, processing the extracted clinical information and the image volume using a customized rendering model, to generate a set of customized rendering parameters for rendering the pathology and a plurality of organs and/or systems surrounding the pathology; and rendering the image volume on a display device, based on the set of customized rendering parameters.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Various aspects of this disclosure may be better understood upon reading the following detailed description and upon reference to the drawings in which.

Figure 1:
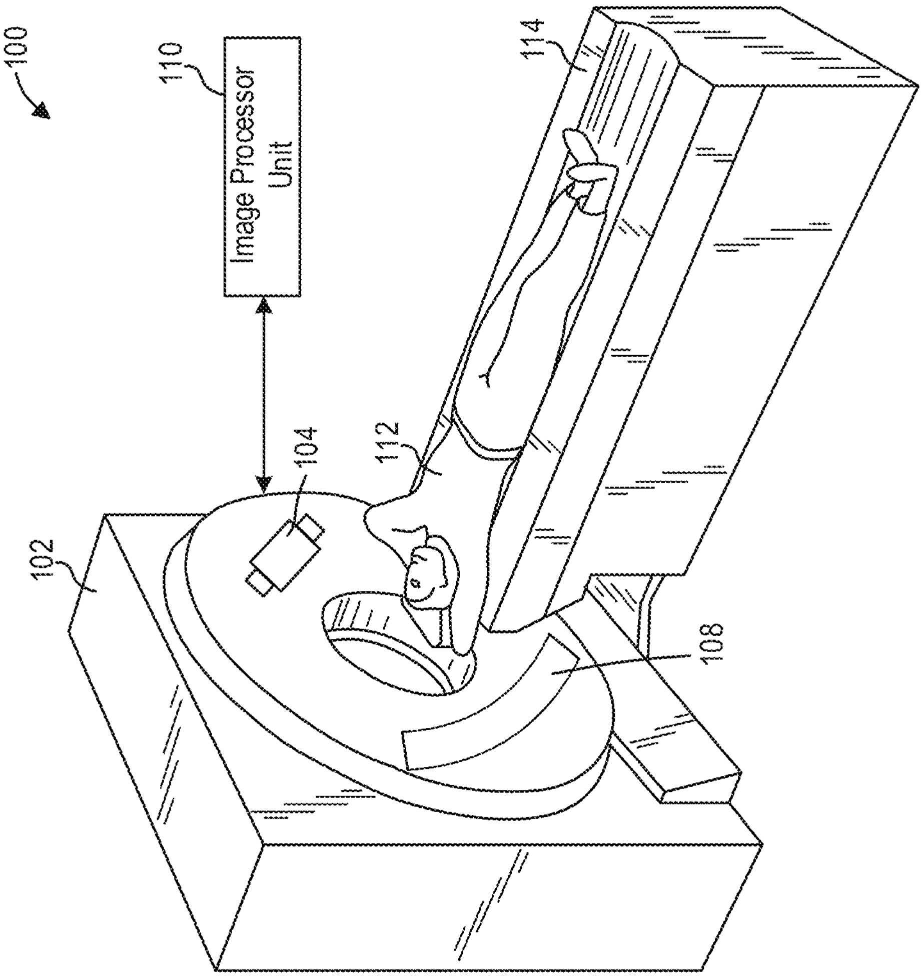
FIG. 1 shows a pictorial view of an imaging system, in accordance with one or more embodiments of the present disclosure.

The drawings illustrate specific aspects of the described systems and methods. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

This description and embodiments of the subject matter disclosed herein relate to methods and systems for medical imaging systems that generate three dimensional (3D) image volumes of scanned objects, such as an anatomy of a patient. While a computed tomography imaging (CT) system is described herein, it should be appreciated that the systems and methods described herein may be used with other types of X-ray imaging systems without departing from the scope of this disclosure. For example, the systems and methods may be used with a magnetic resonance (MR) imaging system, a positron emission tomography (PET) system, a Gemstone Spectral Imaging System (GSI), or a different kind of imaging system.

In an X-ray imaging system, typically an X-ray source emits a fan-shaped beam or a cone-shaped beam towards an object, such as a patient. In some X-ray imaging systems, such as in CT systems, the X-ray source and the detector array are rotated about a gantry within an imaging plane and around the patient, and images are generated from projection data at a plurality of views at different view angles. In other X-ray imaging systems, the X-ray source and the detector array may have a fixed position.

The beam, after being attenuated by the patient, impinges upon an array of radiation detectors. The X-ray detector or detector array typically includes a collimator for collimating X-ray beams received at the detector, a scintillator disposed adjacent to the collimator for converting X-rays to light energy, and photodiodes for receiving the light energy from the adjacent scintillator and producing electrical signals therefrom. An intensity of the attenuated beam radiation received at the detector array is typically dependent upon the attenuation of the X-ray beam by the patient. Each detector element of a detector array produces a separate electrical signal indicative of the attenuated beam received by each detector element. The electrical signals are transmitted to a data processing system for analysis. The data processing system processes the electrical signals to facilitate generation of an image.

In x-ray projection systems, a contrast between target objects and background objects is formed by differences in x-ray attenuation between target and background materials. Larger differences in x-ray attenuation translate to improved differentiation (e.g., higher contrast) of the target materials from the background materials. However, typically, images contain multiple materials and mixtures of materials that may yield similar contrasts in an x-ray projection or reconstructed CT image and make differentiation of the target objects difficult.

Conventional imaging can create a visualization of the density of the tissue and substances imaged in the subject. The density is derived as related to x-ray attenuation of the tissue and is encoded as a grey scale value in order to form an image. Density information is often used to segment regions of the images and associate those regions with certain biological tissues. For example, high attenuation is often associated with bone. By performing segmentation based on density information, it is possible to distinguish the regions in the visualization. For example, the regions may be colored or shaded differently, or bone may be removed from the image so as to generate a soft-tissue image.

Additionally, after an image volume of a patient anatomy has been reconstructed from projection data acquired via an imaging system, one or more AI algorithms may be applied to the image volume to identify and/or extract pathology findings (also referred to herein as findings) from the image volume, such as nodules, calcium scoring, tumors, screws, etc. A radiologist (or caregiver) may examine the findings in detail to determine whether pathologies are present, and to determine a severity of the pathologies. The radiologist may view the image volume within a software application for viewing the results, which may allow the radiologist to rotate the image volume around different axes and/or select one or more cross-sections of the image volume for viewing.

In some cases, the regions and findings may be rendered in a manner that distinguishes the regions and findings from other anatomical features of the patient anatomy. For example, features such as nodules or tumors may be rendered as solid objects, and different organs including the nodules or tumors may be rendered in a translucent fashion with different shadings or colors such that the different organs may be identified. However, in various view angles of the image volume, multiple translucent regions may be "stacked", where a solidly-rendered feature of interest may be within or behind two or more translucent regions, which may have an additive effect that obscures or clouds a view of the feature of interest. As a result, details of the feature of interest may be difficult to see. Additionally, the radiologist may have to manipulate or rotate the image volume in various ways in a trial and error fashion to determine a viewing angle that most clearly shows the feature of interest.

To address this, methods and systems are disclosed herein for automatically enhancing a 3D visualization of features of interest with respect to surrounding anatomical features. The features of interest may include findings and organs found by one or more AI algorithms. Information may first be extracted on regions which have a high probability of developing pathologies. This information could include a severity of the pathology, one or more organs affected by a given finding, and features of the pathology, such as size or thickness, etc. From this information, a view angle that most clearly shows the pathology may be automatically determined, and optimal rendering parameters for each finding/pathology/region (transparency, color of the organ, use of mesh, etc.) may be automatically selected.

Referring now to the figures, FIG. 1 illustrates an exemplary X-ray system 100 configured for CT imaging. It should be appreciated that in other embodiments, X-ray system 100 may be a different type of X-ray imaging system. The X-ray system 100 is configured to image a subject 112 such as a patient, an inanimate object, one or more manufactured parts, and/or foreign objects such as dental implants, stents, and/or contrast agents present within the body. In one embodiment, the X-ray system 100 includes a gantry 102, which in turn, may further include at least one X-ray source 104 configured to project a beam of X-ray radiation 106 (see FIG. 2) for use in imaging the subject 112 laying on a table 114. Specifically, the X-ray source 104 is configured to project the X-ray radiation beams 106 towards a detector array 108 positioned on the opposite side of the gantry 102. Although FIG. 1 depicts a single X-ray source 104, in certain embodiments, multiple X-ray sources and detectors may be employed to project a plurality of X-ray radiation beams for acquiring projection data at different energy levels corresponding to the patient. In some embodiments, the X-ray source 104 may enable dual-energy gemstone spectral imaging (GSI) by rapid peak kilovoltage (kVp) switching. In some embodiments, the X-ray detector employed is a photon-counting detector which is capable of differentiating X-ray photons of different energies. In other embodiments, two sets of X-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the X-ray system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some CT imaging system configurations, an X-ray source projects a cone-shaped X-ray radiation beam which is collimated to lie within an X-Y-Z plane of a Cartesian coordinate system and generally referred to as an "imaging plane." The X-ray radiation beam passes through an object being imaged, such as the patient or subject. The X-ray radiation beam, after being attenuated by the object, impinges upon an array of detector elements. The intensity of the attenuated X-ray radiation beam received at the detector array is dependent upon the attenuation of an X-ray radiation beam by the object. Each detector element of the array produces a separate electrical signal that is a measurement of the X-ray beam attenuation at the detector location. The attenuation measurements from all the detector elements are acquired separately to produce a transmission profile.

In some CT systems, the X-ray source and the detector array are rotated with a gantry within the imaging plane and around the object to be imaged such that an angle at which the X-ray beam intersects the object constantly changes. A group of X-ray radiation attenuation measurements, e.g., projection data, from the detector array at one gantry angle is referred to as a "view." A "scan" of the object includes a set of views made at different gantry angles, or view angles, during one revolution of the X-ray source and detector.

The X-ray source 104 includes an anode and a cathode. Electrons emitted by the cathode (e.g., resulting from energization of the cathode) may be intercepted by a target arranged at or near the anode. Electrons intercepted by the target may release energy in the form of X-rays, with the X-rays being directed toward the detector array 108. An area of the target surface that receives the electrons from the cathode and forms the emitted X-rays may be referred to herein as a focal spot. The emitted X-rays may be focused on a portion of the scanned subject 204, at an effective focal spot.

Figure 2:
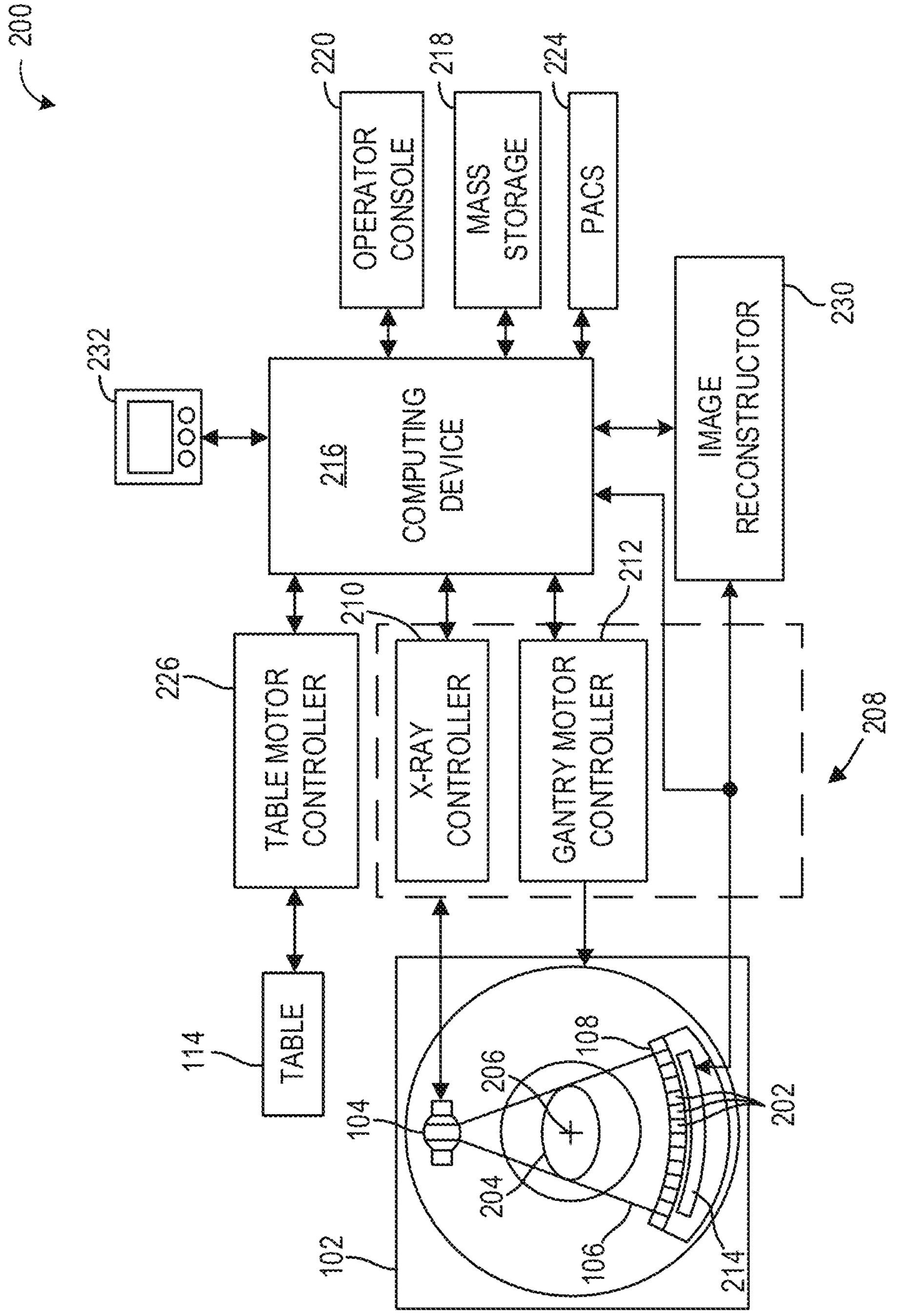
FIG. 2 shows a block schematic diagram of an exemplary imaging system, in accordance with one or more embodiments of the present disclosure.

FIG. 2 illustrates an exemplary X-ray imaging system 200 similar to the X-ray system 100 of FIG. 1. In accordance with aspects of the present disclosure, the X-ray imaging system 200 is configured for imaging a subject 204 (e.g., the subject 112 of FIG. 1). In one embodiment, the X-ray imaging system 200 includes the detector array 108 (see FIG. 1). The detector array 108 further includes a plurality of detector elements 202 that together sense the X-ray radiation beam 106 (see FIG. 2) that pass through the subject 204 (such as a patient) to acquire corresponding projection data. In some embodiments, the detector array 108 may be fabricated in a multi-slice configuration including the plurality of rows of cells or detector elements 202, where one or more additional rows of the detector elements 202 are arranged in a parallel configuration for acquiring the projection data.

In certain embodiments, the X-ray imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the X-ray source 104 and the detector array 108 rotate, the detector array 108 collects data of the attenuated X-ray beams. The data collected by the detector array 108 undergoes pre-processing and calibration to condition the data to represent the line integrals of the attenuation coefficients of the scanned subject 204. The processed data are commonly called projections. In some examples, the individual detectors or detector elements 202 of the detector array 108 may include photon-counting detectors which register the interactions of individual photons into one or more energy bins. It should be appreciated that the methods described herein may also be implemented with energy-integrating detectors.

In one embodiment, the X-ray imaging system 200 includes a control mechanism 208 to control movement of the components such as rotation of the gantry 102 and the operation of the X-ray source 104. In certain embodiments, the control mechanism 208 further includes an X-ray controller 210 configured to provide power and timing signals to the X-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device or mass storage device 218. The storage device 218, for example, may be any type of non-transitory memory and may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the X-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates one operator console 220, more than one operator console may be coupled to the X-ray imaging system 200, for example, for inputting or outputting system parameters, requesting examinations, plotting data, and/or viewing images. Further, in certain embodiments, the X-ray imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the X-ray imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized X-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the X-ray imaging system 200 and instead the computing device 216 may perform one or more functions of the image reconstructor 230. Moreover, the image reconstructor 230 may be located locally or remotely, and may be operatively connected to the X-ray imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

Figure 3:
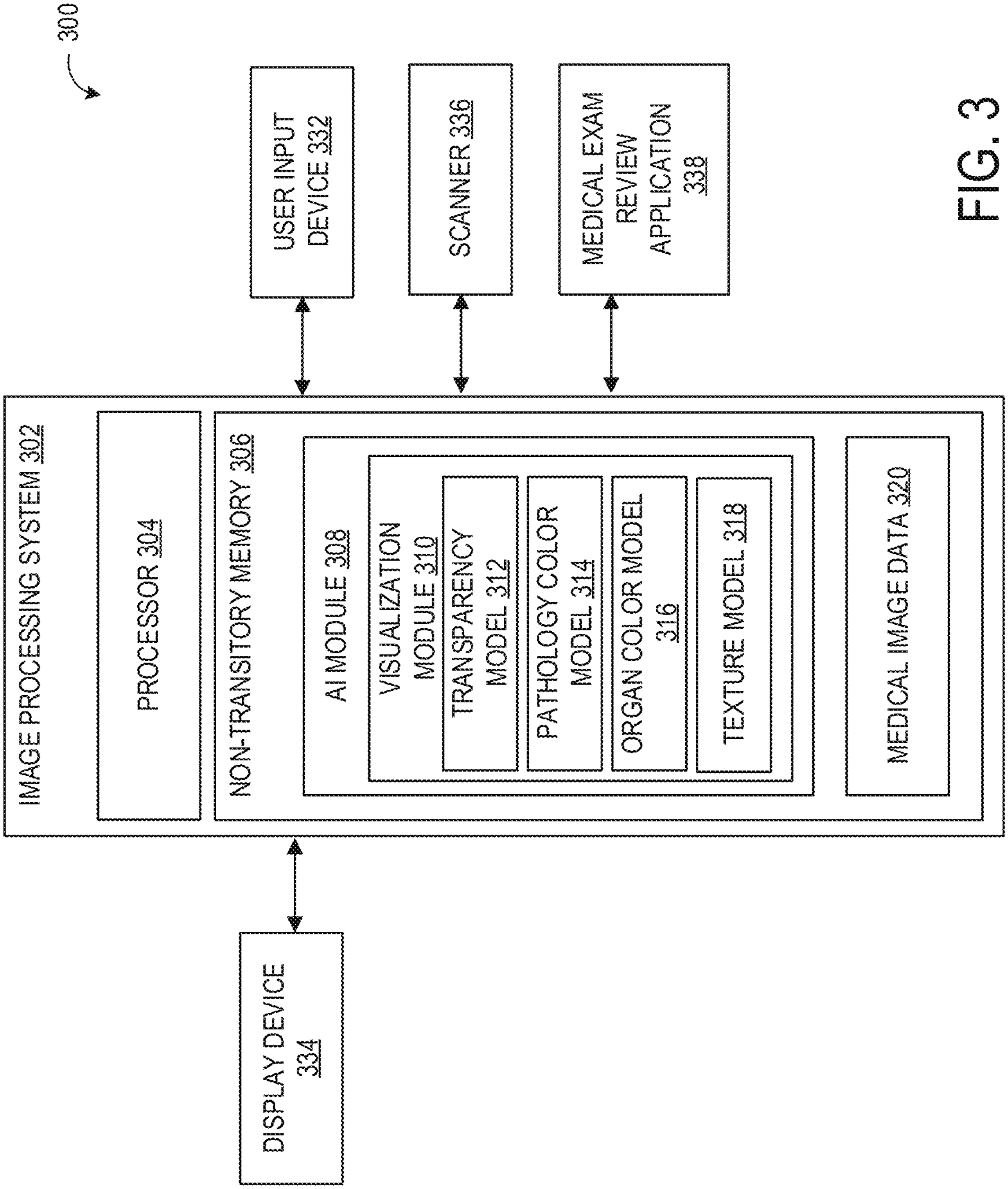
FIG. 3 shows a schematic diagram of an image processing system, in accordance with one or more embodiments of the present disclosure.

Referring now to FIG. 3, an exemplary image processing system 302 of a medical imaging system 300 is shown, where medical imaging system 300 may be a non-limiting example of X-ray imaging system 200 of FIG. 2 and/or the X-ray system 100 of FIG. 1. Image processing system 302 may include or be included within image processor unit 110 of FIG. 1, for example. In other embodiments, image processing system 302 may be included in or coupled to a different kind of imaging system (e.g., PET, GSI, MRI, etc.).

In some examples, at least a portion of image processing system 302 is disposed at a device (e.g., edge device, server, etc.) communicably coupled to the medical imaging system 300 via wired and/or wireless connections. In some embodiments, at least a portion of image processing system 302 is disposed at a separate device (e.g., a workstation) which can receive images from the medical imaging system 300 or from a storage device which stores the images/data generated by the medical imaging system 300.

Image processing system 302 includes a processor 304 configured to execute machine readable instructions stored in non-transitory memory 306. Processor 304 may be single core or multi-core, and the programs executed thereon may be configured for parallel or distributed processing. In some embodiments, the processor 304 may optionally include individual components that are distributed throughout two or more devices, which may be remotely located and/or configured for coordinated processing. In some embodiments, one or more aspects of the processor 304 may be virtualized and executed by remotely-accessible networked computing devices configured in a cloud computing configuration.

Non-transitory memory 306 may store at least an AI module 308 and medical image data 320. AI module 308 may include various AI models and algorithms that may be applied to image data received from imaging system 300. The various AI models may include probabilistic models, statistical models, rules-based models, as well as machine learning (ML) and/or deep learning (DL) neural network models, and instructions for implementing the AI, ML and/or DL models to perform various tasks on medical images generated by imaging system 300. For example, the AI models may be used to detect, identify, segment, label, and/or extract features of the medical images, including anatomical features (e.g., organs, systems, vessels, arteries, bones, etc.) and findings (e.g., tumors, nodules, lesions, scarring, etc.), as described in greater detail herein. In some examples, AI module 308 includes instructions for implementing one or more gradient descent algorithms, applying one or more loss functions, and/or training routines, for use in adjusting parameters of the ML and/or DL models.

AI module 308 may further include a visualization module 310, which may include various instructions and/or routines for visualizing medical images acquired using a scanner 336 of medical imaging system 300. In particular, visualization module 310 may include instructions for one or more methods for enhancing 3D visualizations of the medical images, such as method 400 described below in reference to FIGS. 4A and 4B. The medical images may include 2D images and 3D image volumes, such as CT image volumes, MRI image volumes, and the like. Visualization module 310 may apply one or more AI models of AI module 308 to the medical images prior to displaying the medical images on a display device, and/or during the displaying of the medical images, to achieve various visualization goals described herein.

In particular, visualization module 310 may include a transparency model 312, a pathology color model 314, an organ color model 316, and a texture model 318, which may be used to determine various rendering parameters for displaying an image volume. The rendering parameters may be set to highlight one or more anatomical regions visible in the image volume, and to highlight pathology findings in or on the anatomical regions, in a way that efficiently communicates information about a size, extent, severity, or other characteristic of the pathology findings. In various embodiments, the pathology findings may be generated by an AI model of AI module 308.

Transparency model 312, pathology color model 314, organ color model 316, and texture model 318 may be one of various types of models that take an image volume as input and output a set of rendering parameters corresponding to the model type. In various examples, one or more of transparency model 312, pathology color model 314, organ color model 316, and texture model 318 may be rules-based models that determine suitable rendering parameters by applying a series of conditions or criteria. For example, a decision tree or probabilistic model may be used. In other embodiments, statistical models or other types of models may be used. In some examples, one or more machine learning (ML) algorithms may additionally or alternatively be used.

Transparency model 312 may take the pathology findings and the image volume as input, and output sets of one or more transparency rendering parameters that define a translucence of one or more regions and/or findings (e.g., pathologies) in the image volume. In some examples, anatomical segmentations of portions of the image volume may be additional inputs into transparency model 312. In one embodiment, transparency model 312 is an AI model.

For example, a first set of transparency rendering parameters outputted by transparency model 312 may render the pathology findings as solid volumes. A second set of transparency rendering parameters outputted by transparency model 312 may render one or more organs affected by the pathology findings with a first translucence, where the first translucence allows boundaries and characteristics of the affected organs to be visible, while affording a clear view of the (solid) pathology findings. A third set of transparency rendering parameters outputted by transparency model 312 may render other organs and/or anatomical structures/regions that are not affected by the pathology findings with a second, greater translucence, such that the unaffected organs are less visible, in order not to obscure or distract a viewer from the clear view of the (solid) pathology findings. In one example, a fourth set of transparency rendering parameters outputted by transparency model 312 may not render the unaffected organs, such that the rendered, affected organs and findings are more easily visualized.

Additionally or alternatively, transparency model 312 may apply one or more transparency schemes or formulas to adjust a transparency of different portions of the image volume. For example, portions of the image volume closest to a pathological finding or anatomical landmark may be assigned a first, lower set of transparency settings, and portions of the image volume farther from the pathological finding or anatomical landmark may be assigned a second, higher set of transparency settings. In some examples, the transparency of the portions of the image volume may be adjusted on a voxel-by-voxel basis, where a voxel is assigned a transparency setting (e.g., a set of transparency rendering parameters) by transparency model 312 as a function of a distance between the voxel and the pathological finding or anatomical landmark. In this way, a visibility of anatomical features surrounding the pathological finding that are unaffected by the pathological finding may be reduced, so not to obscure the pathology findings. In other examples, a different transparency scheme may be used.

Pathology color model 314 may be an AI model that takes the pathology findings and/or the image volume as input, and outputs one or more rendering parameters for assigning a color to the pathology findings. For the purposes of this disclosure, the color may include a hue, shading, or degree of illumination (e.g., brightness) of the color, or similar means of highlighting an element. In various embodiments, the color may be assigned based on a gradient between two reference colors, based on a severity of the pathology findings. For example, the gradient may be a yellow-red gradient, and a malignant tumor may be assigned a red color, while a benign tumor may be assigned a yellow color, or a color on the yellow-red gradient may be assigned based on a stage of the tumor, where a later-stage tumor may be assigned a more red color, and an earlier-stage tumor may be assigned a more yellow color. In other embodiments, a different color scheme may be applied by pathology color model 314.

Organ color model 316 may be an AI model that takes the pathology findings and/or the image volume as input, and outputs one or more rendering parameters for assigning a color to one or more organs affected by the pathology findings. In various embodiments, the color may be assigned based on a degree to which the pathology findings affect the functioning of a respective organ. That is, a first organ may be assigned a first color to indicate that the first organ is affected by the pathology findings to a first degree; a second organ may be assigned a second color to indicate that the second organ is affected by the pathology findings to a second, different degree; and so on. For example, the pathology findings may include nodules detected on both lungs of a patient, where a first nodule on a first lung of the lungs has a first, larger size, and a second nodule on a second lung of the lungs has a second, smaller size. Organ color model 316 may output a first rendering parameter assigning a first color to the first lung, and output a second rendering parameter assigning a second color to the second lung, thereby indicating that a functioning of the first lung is affected by the first nodule to a greater degree than the second lung is affected by the second nodule. For example, the first color may be a brighter color, indicating a greater severity of the first nodule, and the second color may be a darker color, indicating a lesser severity of the second nodule. Alternatively, the first color may be a more red color, and the second color may be a more yellow color, indicating the severity of the nodules on the red-yellow gradient. In still other examples, a different color scheme may be used by organ color model 316.

Texture model 318 may be an AI model that takes the pathology findings and/or the image volume as input, and outputs one or more rendering parameters for assigning a texture to a surface one or more organs affected or unaffected by the pathology findings. The texture may be selected to highlight or diminish a presence of an organ in the rendered image volume. For example, a first organ that obscures the pathology findings may be rendered with a mesh surface by texture model 318, such that the pathology findings may be viewed through the first organ. A second organ that is impacted by the pathology findings may be rendered with a textured surface. A third organ that is not impacted by the pathology findings may be rendered with a smooth, or different type of surface. In this way, the texture may be advantageously used to communicate information about the pathology findings to the viewer, while also making it easier to visualize anatomical features or structures of interest.

It should be appreciated that the examples provided herein are for illustrative purposes, and in other embodiments, different types of visualization models may be used to distinguish between the anatomical features or structures of interest without departing from the scope of this disclosure. Additionally, the visualization models described herein may use color, texture, transparency, and/or other types of parameters in different ways than those described above.

Medical image data 320 may include images acquired by imaging system 300. Medical image data 320 may include for example, medical images acquired via a scanner 336, which may be an MRI scanner, a CT scanner, a scanner for spectral imaging, or via a different imaging modality of the imaging system 300. Scanner 336 may be any imaging device configured to image a subject such as a patient, an inanimate object, one or more manufactured parts, and/or foreign objects such as dental implants, stents, and/or contrast agents present within the body. Image processing system 302 may receive imaging data from scanner 336, process the received imaging data via processor 304 based on instructions stored in one or more modules of non-transitory memory 306, and/or store the received and/or processed imaging data in medical image data 320. The medical images and imaging data stored as medical image data 320 may be processed based on instructions stored in visualization module 310, and may be processed by one or more AI models stored in AI module 308.

Image processing system 302 may be operably/communicatively coupled to a user input device 332 and a display device 334. User input device 332 may comprise one or more of a touchscreen, a keyboard, a mouse, a trackpad, a motion sensing camera, or other device configured to enable a user to interact with and manipulate data within image processing system 302. Display device 334 may include one or more display devices utilizing virtually any type of technology. In some embodiments, display device 334 may comprise a computer monitor, and may display medical images. Display device 334 may be combined with processor 304, non-transitory memory 306, and/or user input device 332 in a shared enclosure, or may be peripheral display devices and may comprise a monitor, touchscreen, projector, or other display device known in the art, which may enable a user to view medical images produced by medical imaging system 300, and/or interact with various data stored in medical image data 320 and non-transitory memory 306. In some examples, the display device 334 may be the same as or similar to display device 232 of FIG. 2.

Image processing system 302 may be operably/communicatively coupled to a medical exam review application 338. That is, in some examples, image processing system 302 may be used to render aspects (e.g., findings) of an image volume that is acquired by the X-ray imaging system for display on display device 334 in real time, meaning, at a time of the acquisition. In other examples, the image volume may be acquired at a first time, and stored, to be viewed at a second, later time by a caregiver or radiologist. For example, the caregiver may open the image volume in medical exam review application 338 on a computer or workstation of the caregiver or of a healthcare system, and the caregiver may use image processing system 302 to generate an enhanced visualization of the image volume. In some examples, the image processing system may be installed on the computer or workstation, or incorporated into medical exam review application 338.

It should be understood that image processing system 302 shown in FIG. 1 is for illustration, not for limitation. Another appropriate image processing system may include more, fewer, or different components.

Figure 4A:
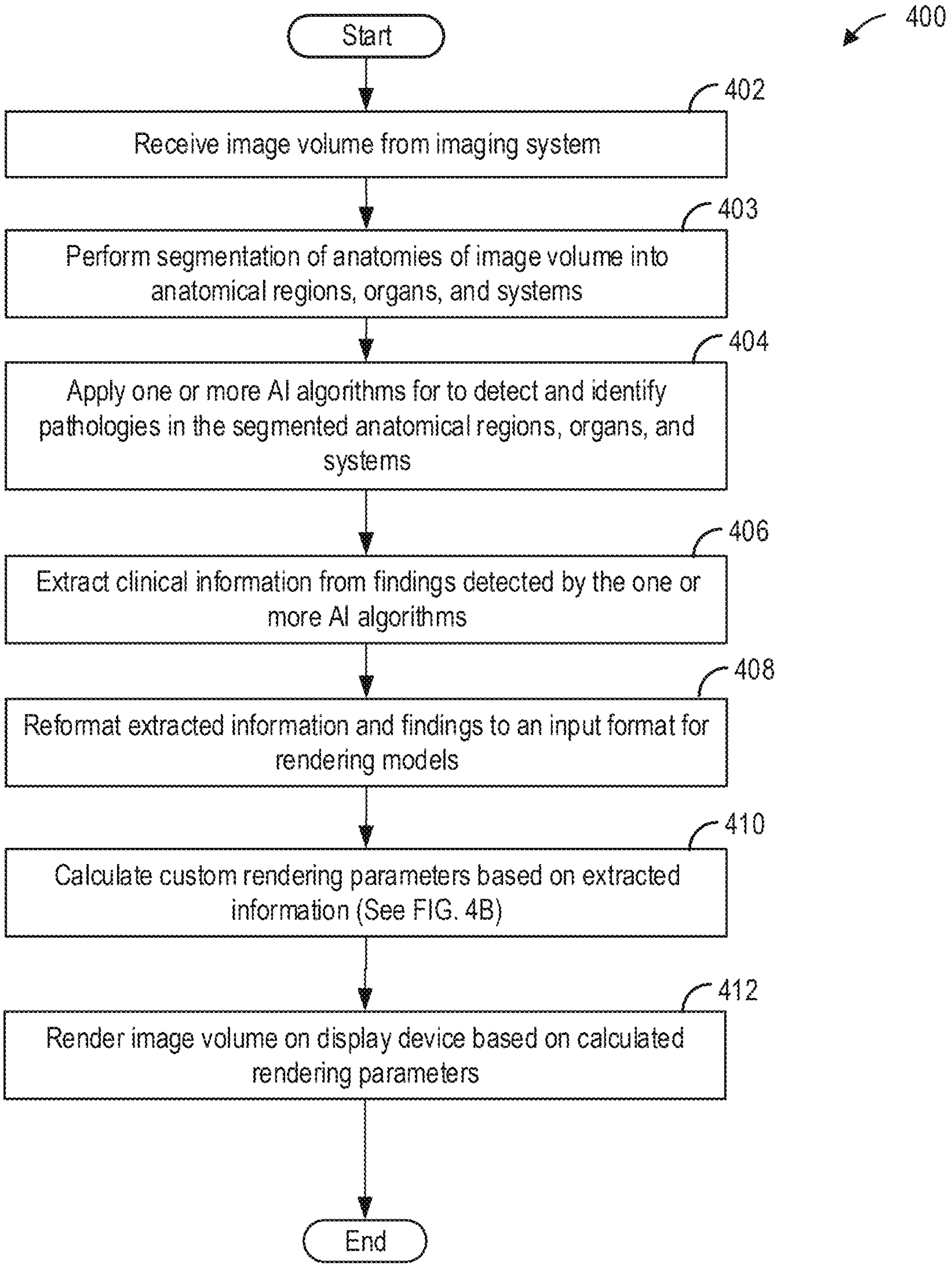
FIG. 4A is a flowchart illustrating an exemplary high-level method for generating enhanced visualizations of regions of a medical image volume, in accordance with one or more embodiments of the present disclosure.

Referring now to FIG. 4A, a method 400 is shown for generating an enhanced visualization of select regions and findings of a medical image volume, where the enhanced visualization may show the select regions and findings with a greater degree of clarity and detail than may be achieved using other, conventional visualizations. Method 400 and other methods described herein may be executed by a processor of an image processing system of a medical imaging system, such as image processing system 302 of FIG. 3.

Method 400 begins at 402, where the method includes receiving an image volume of an anatomy of a patient from the medical imaging system. The image volume may be a CT image volume, an MR imaging volume, or an image volume reconstructed from projection data acquired via a different type of imaging system.

At 403, the method may include performing a segmentation of anatomies of the image volume into distinct anatomical regions, organs, and/or systems. The segmentation may be performed in accordance with various methods and techniques known in the art.

At 404, the method includes applying one or more AI algorithms or models for detecting and/or identifying pathologies present in segmented anatomical regions, organs, and/or systems of the image volume. The one or more AI algorithms or models may detect regions of a skeleton, system, or organs (lungs, heart, prostate, kidney, liver, etc.) of the patient in the image volume. For example, the one or more AI algorithms or models may be applied to segment elements of a circulatory system of the patient, such as a heart, vessels, arteries, etc., or a respiratory system of the patient, such as lungs, airways, etc. The one or more AI algorithms or models may further extract findings such as nodules, calcium scoring, tumors, screws, etc. visible in, on, or around the detected regions of the image volume. The image volume may be inputted into various AI algorithms specific to and/or trained to detect certain types of findings, or findings in certain types of anatomies. For example, the image volume may be inputted into a first AI algorithm which may detect a presence of nodules in lungs of the patient; the image volume may be inputted into a second AI algorithm which may detect a presence of calcium deposits in a heart of the patient; and so on.

The one or more AI algorithms may take as input the image volume, and may output the findings in various ways. The outputted findings may include clinical information, such as a severity of a pathology, one or more different regions that are impacted by the pathology, a location of the pathology in the image volume, and/or other clinical information.

In some examples, an output of an AI algorithm of the one or more AI algorithms may include a voxel-by-voxel identification of the findings within the image volume. That is, an output layer of the AI algorithm may include a 3D matrix of output nodes of the same dimensions as the image volume, where each output node of the 3D matrix of output nodes corresponds to a specific input node of a 3D matrix of input nodes of an input layer of the image volume. In one example, a first set of output nodes corresponding to voxels including the findings may output a first value, and a second set of output nodes corresponding to voxels not including the findings may output a second value (e.g., generating a mask). The first value and the second value may be binary values, such as a one and a zero. The voxels including the findings may then be rendered in a manner that distinguishes the findings from surrounding anatomies, as described in greater detail below.

In other examples, an output of an AI algorithm of the one or more AI algorithms may include one or more, or a list of coordinate points corresponding to center points, boundary points (e.g., a boundary box), or other types of points within the image volume where the findings are present. Additionally or alternatively, the AI algorithm may output an encoding that specifies a type of findings detected. A first encoding may indicate a first type of finding; a second encoding may indicate a second type of finding; and so on. Additional encodings may be outputted that indicate characteristics of the finding, such as a size, location, extent, etc. For example, one AI algorithm may be trained to detect nodules in a lung of the patient, and the AI algorithm may output an encoding including a center point of a nodule, an orientation of the nodule, dimensions of the nodule, an extent of the nodule, and the like. The center point, orientation, dimensions, extent, and/or other aspects included in the encoding may be used to determine a location, size, and characteristics of the nodule in the image volume, so that the nodule may be rendered for viewing.

Additionally, in some examples where original information of the findings is not sufficient for optimal 3D visualization, rather than computing rendering parameters from the encoded characteristics, an additional step may be to create a region of interest (ROI) from the encoded characteristics to compute rendering parameters from this ROI and then apply these rendering parameters to the ROI comprising the findings. For example, a center point, orientation, and dimensions of a lesion may be outputted by the AI algorithm. However, rather than applying rendering parameters to highlight the lesion in the image volume based on the center point, orientation, and dimensions, a spherical ROI may be defined around the center point, and the rendering parameters may be applied to the spherical ROI. By creating the ROI from the encoded characteristics, a visibility of the findings within the image volume may be increased.

At 406, the method includes extracting clinical information relevant to rendering the image volume with respect to each region and finding detected. For a finding, the extracted clinical information may include a severity of the pathology, one or more different regions impacted by the pathology, etc. For an organ, the extracted clinical information may include geometrical properties (size, thickness) of the organ, a position of the organ with respect to a finding, whether the organ is comparable to a reference standard or has clinical anomalies, and the like. The extracted clinical information may be used by one or more customized rendering models, which may render the detected regions and findings in a manner that conveys the extracted clinical information. Each rendering model of the one or more customized rendering models may render a different aspect of the regions and findings. For example, a pathology color model may render a detected pathology based on the severity of the pathology, where a more severe pathology may be rendered with a first shade, color, tone, etc. (e.g., red), and a less severe pathology may be rendered with a second shade, color, tone, etc. (e.g., yellow). In some examples, a color map may be used. For example, the detected pathology may include calcium deposits that may be scored using an Agatston calcium score. The color map may specify different colors based on the calcium scoring. For example, the color may specify that portions of the detected pathology having an Agatston score of 0 may be represented in light green; portions of the detected pathology having an Agatston score between 1-100 may be represented in green; portions of the detected pathology having an Agatston score of 101-300 may be represented in yellow; and portions of the detected pathology having an Agatston score above 300 may be represented in red.

Additionally or alternatively, a transparency rendering model may render the findings and/or surrounding organs in different degrees of transparency based on the severity of the findings, or a different rendering model may be used. In this way, the severity of the pathology may be quickly and efficiently visually communicated to a user of the image processing system, without having to rely on textual or other types of communication. Clinical information included in an output of an AI algorithm that is not relevant to rendering the image volume may not be extracted.

At 408, the method optionally includes reformatting and/or encoding the extracted information and findings to an input format used by one or more rendering models. Because various AI algorithms may be used to detect different types of pathologies, and each AI algorithm may output findings in a different manner, the various output formats may be reformatted into a common, shared format that may be relied on by each of the one or more rendering models. That is, each rendering model of the one or more rendering models may expect finding input data to conform to a predefined format. Once the various findings in the various output formats have been reformatted into the predefined, common format, the findings may be inputted into each of the one or more rendering models in a similar manner. By reformatting the output formats in this manner, a processing of the findings by the one or more rendering models may be performed more efficiently and rapidly than if each of the one or more rendering models relied on inputs of a different format, or if the output formats were reformatted individually for each rendering model of the one or more rendering models. By processing the findings more efficiently and rapidly, an amount of computational and memory resources relied on for the processing may be reduced, increasing a functionality of the image processing system.

As an example, an AI algorithm may output a segmentation of an image volume into regions, including a segmentation of a nodule detected on a lung of the image volume (e.g., the findings); a list of coordinates (e.g., an array of voxel positions defining the coordinates) that define a bounding box of the nodule in the image volume; and a first encoding of a severity of the nodule on a scale of 1 to 100. The standardized input format may include the segmentation of the image volume into regions, with the segmented nodule. However, the standardized input format may rely on a center point of the nodule and a diameter of the nodule. The list of coordinates that define the bounding box may be used to determine the center point of the nodule and the diameter of the nodule, such that the location and extent of the nodule may be converted from a bounding-box description into the standardized input format. The standardized input format may also rely on an encoding of the severity of the nodule on a scale of 1 to 10. To reformat the output of the AI algorithm into the standardized input format, the first encoding of the severity of the nodule on the scale of 1 to 100 may be converted to a second encoding of the severity of the nodule on a scale of 1 to 10. The segmentation of the image volume and nodule, the center point and diameter of the nodule, and the second encoding of the severity of the nodule may be inputted into rendering model, as described below, in accordance with the expected standardized input format. For example, the standardized input format may be defined by the following pseudo code:

```
"Region 1": {                                                    (1)
  "Segmentation": Array voxelwise (same size as input volume)
    "Findings": {
        "Finding 1 name": {
            "segmentation": array | None, [required]
          "center point": value, [required]
          "severity": range between 1 and 10 [required],
          ... }
    }
  }
```

At 410, the method includes calculating customized rendering parameters based on the extracted information. The customized rendering parameters may be computed automatically for each organ and each finding. The customized rendering parameters may include a transparency/opacity, color, and/or shading of each organ/finding, parameters for establishing a camera position (e.g., a view angle from which to view the image volume), and/or other parameters. Calculating the customized rendering parameters is described in greater detail below in reference to FIG. 4B.

At 412, once rendering parameters are computed for each finding and organ, the method includes rendering the image volume on a display device, based on the calculated customized rendering parameters. It should be appreciated that steps 406-410 may be performed prior to rendering the image volume on the display device. That is, the image volume is not rendered a first time, and then re-rendered in accordance with the calculated customized rendering parameters. Rather, the image volume is not rendered for display on the display device until the customized rendering parameters have been calculated. In this way, computational resources used by the image processing system to render the image volume may be reduced, for example, by selectively rendering some organs or systems of the image volume with a mesh texture, with high transparency, etc.

Figure 4B:
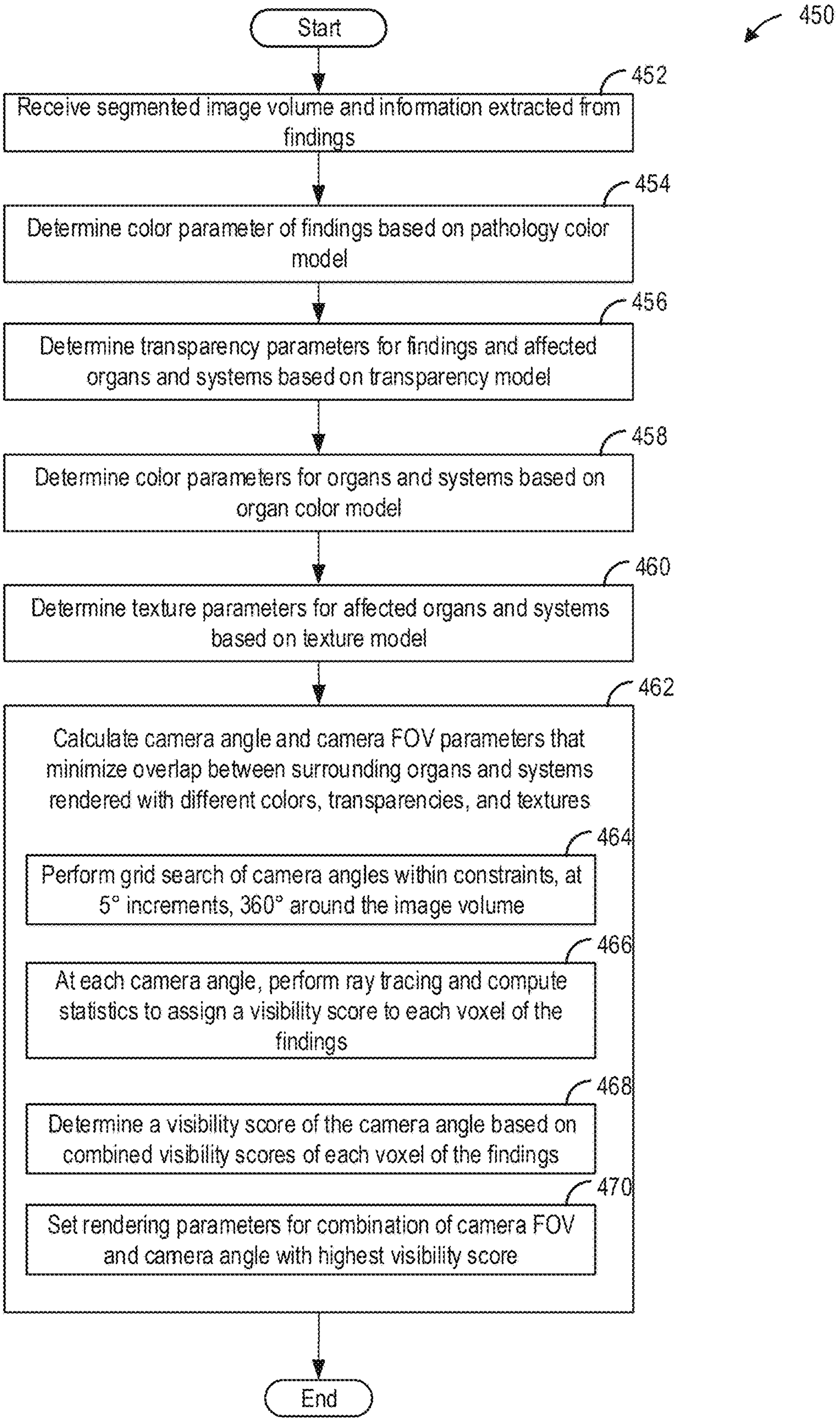
FIG. 4B is a flowchart illustrating an exemplary method for determining a set of rendering parameters for rendering an enhanced visualization of regions of a medical image volume, in accordance with one or more embodiments of the present disclosure.

FIG. 4B shows a method 450 for calculating a set of customized rendering parameters for displaying an enhanced visualization of select regions and findings of a medical image volume of a patient, in accordance with an embodiment. In various examples, method 450 may be performed as part of method 400 described above in reference to FIG. 4A.

The customized rendering parameters may be determined by inputting the image volume and clinical information about the findings into one or more rendering models. In the embodiment described herein, the image volume and clinical information about the findings may be inputted into a plurality of rendering models, where each of the rendering models outputs a set of rendering parameters for displaying one or more aspects of the select regions and findings. For example, a first rendering model may output a first set of rendering parameters for rendering a transparency of the regions and findings; a second rendering model may output a second set of rendering parameters for rendering a color of the regions and findings; a third rendering model may output a third set of rendering parameters for rendering a texture of the regions and findings; and so on. As described above, the rendering models may be implemented in various ways, such as decision trees, probabilistic or statistical models, rules-based models, ML models, or a different type of model. With respect to the described embodiment, it should be appreciated that an order of applying the rendering models may vary, and as such, in other embodiments, the steps of method 450 may be applied in a different order.

Method 450 begins at 452, where the method includes receiving a segmented image volume and clinical information extracted from the findings from the image volume. The extracted clinical information may include a number and a position of various pathologies of the findings, a severity of the various pathologies, etc., as described above in reference to FIG. 4A. The extracted clinical information may include information about how one or more organs and/or systems of the patient are impacted by the findings. For example, if calcium deposits are detected on a heart of a patient, the extracted clinical information may include an assessment of a risk of heart disease of the patient as a result of the calcium deposits. The assessment of the risk may include, for example, a risk score (e.g., on a scale of 1 to 10). The extracted clinical information may be reformatted and/or encoded into a common, predefined format for applying one or more rendering models, as described above, where the predefined format may include the risk score.

At 454, the method includes determining one or more color rendering parameters of the findings to display the findings in a selected color. The one or more rendering parameters may be determined by a pathology color model, such as pathology color model 314 of FIG. 3. The pathology model may take as input the segmented image volume and the reformatted/encoded extracted clinical information corresponding to the findings, and may output one or more rendering parameters for rendering the findings in the color determined by the pathology color model. The one or more rendering parameters for rendering the findings in the color may include rendering parameters for color tone, hue, brightness, contrast, shading, intensity, etc. The color rendering parameters may reflect a severity of a pathology of the findings. For example, if the findings include a tumor that is malignant, the tumor may be rendered in a red color, and if the tumor is benign, the tumor may be rendered in a yellow color. In other examples, different colors may be used. In some examples, a set of candidate colors, or preferred colors, may be specified in a lookup table consulted by the pathology color model. Additionally, the color determined by the pathology color model may be a color gradient between a first color and a second color. For example, a red-yellow color gradient may be used, where the findings are rendered in a more red color as a severity of the findings increases.

At 456, method 450 includes determining one or more rendering parameters for rendering a transparency of the findings and/or organs and/or systems of the patient, including the one or more organs and/or systems that are affected by the findings, and other organs and/or systems that are unaffected by the findings. In other words, different anatomical regions of patient included in the image volume may be rendered on a display screen (e.g., display device 232 or display device 334) with differing degrees of transparency, to facilitate visualization of the findings.

For example, the findings may include nodules located on lungs of the patient. The nodules (e.g., a region of interest) may be rendered as solid volumetric objects in the image volume, such that aspects and characteristics of the nodules may be easily seen and/or measured. However, rib bones of the patient may obscure the nodules in some perspective views of the image volume. To ensure that the rib bones do not obscure the nodules, and to increase a range of view angles from which the nodules may be viewed, the rib bones may be rendered with a first degree of transparency that allows the nodules to be viewed when behind portions of the rib bones. Additionally, the nodules may be located on a side of a lung, such that the nodules may be obscured by portions of the lung in certain view angles of the image volume. To facilitate viewing the nodules even from a view angle where the lung obscures the nodules, the lungs may be rendered with a second degree of transparency, such that the nodules may be seen through the lung. The second degree of transparency may be the same as the first degree of transparency, or the second degree of transparency may be greater than the first degree of transparency (e.g., where the lung is more transparent than the rib bones), or the second degree of transparency may be less than the first degree of transparency (e.g., where the rib bones are more transparent than the lung).

In various embodiments, the first degree of transparency, the second degree of transparency, and other degrees of transparency of other organs and systems of the patient may be determined by a transparency model, such as transparency model 312. The transparency model may take as input an encoding of the findings (e.g., in the predefined format) and the segmented image volume, and may output one or more sets of rendering parameters controlling the transparency of the findings and other regions, organs, and systems included in the image volume. In various embodiments, the transparency model may apply a series of pre-established rules to the extracted clinical information to generate the rendering parameters.

In some examples, the transparency model may minimize a degree of transparency of an organ or system to allow a pathology (e.g., the nodules, etc.) to be seen through the organ or system. Minimizing the degree of transparency of the organ or system may include rendering the organ or system with a transparency high enough that the organ or system may be barely visible or invisible. For example, an organ or system that is unaffected by the pathology may be rendered barely visible to focus an attention of a viewer on the pathology and affected organs or systems. Additionally, by rendering the organ or system barely visible or invisible, an amount of computation relied on by the image processing system to render the image volume may be reduced, resulting in a faster and more efficient display of the image volume.

In some examples, the transparency model may be used to determine transparency parameters for individual voxels of the image volume. As described above in reference to FIG. 3, a formula may be used to generate the transparency parameters as a function of one or more variables, such as, for example, a distance from a voxel to a finding. In other words, voxels including the findings may be rendered with a minimum transparency (e.g., as solid regions); voxels including regions or systems that are not of interest may be rendered with high transparency (e.g., close to 100% transparent); and for voxels including impacted regions, voxels that are closer to a pathology may be rendered with less transparency than voxels that are farther from the pathology.

At 458, the method includes determining color rendering parameters for the segmented organs and systems of the patient, using an organ color model (e.g., organ color model 316). The organ color model may determine appropriate colors to be applied to the organs and systems affected by the pathology (e.g., rather than the pathology itself) to most efficiently highlight the findings and affected organs and systems. For example, the affected organs and systems may be assigned a first color, or set of colors, and unaffected organs and systems may be assigned a second color or set of colors. In some cases, the findings may include a degree to which an organ or system is affected, and one or more color rendering parameters may display the organ or system in a color (shade, tone, hue, intensity, etc.) that reflects the degree.

At 460, the method includes determining texture rendering parameters used to render the affected organs and systems, using a texture model (e.g., texture model 318). The texture rendering parameters may be used, for example, to render a surface of an affected organ or system using a mesh. An advantage of the mesh rendering is that contours of the affected organ or system may be clearly visualized, while allowing the findings (e.g., pathologies) within the affected organ or system to be seen through the mesh. In contrast, if transparency rendering parameters are used to render the affected organ or system with a degree of transparency to allow the findings to be seen, the contours of the affected organ or system may not be clearly visualized.

The texture rendering parameters may include one or more parameters for rendering the affected organ or systems with a mesh of a specific resolution, where the resolution may be adjusted by the texture model. For example, in a first scenario, the mesh may be rendered as a tight mesh with a higher resolution, which may show contours of the affected organ or system in greater detail. In a second scenario, the mesh may be rendered with a lower resolution with more sparsely drawn lines, which may allow the findings to be more easily seen through the affected organ or system. In this way, the texture rendering parameters may be adjusted to increase either or both of a visibility of the findings and an amount of clinical information communicated via the visualization.

At 462, the method includes calculating camera angle and camera field of view (FOV) rendering parameters that define an optimal camera angle for viewing the findings, such that each pathology identified is maximally visible and an overlap between the findings and surrounding organs and systems rendered with different colors, transparencies, and textures is minimized. Calculating the camera angle and camera FOV rendering parameters that define the optimal camera angle may include, at 464, selecting a plurality of candidate FOVs, and for each FOV, performing a grid search of a plurality of camera angles around the image volume at small camera angle increments. For example, the camera angle increments may be 5 degree increments around one or more axes, where camera angles are assessed at every 5° over 360° of the image volume.

At 466, at each camera angle, calculating the camera angle and camera FOV rendering parameters includes performing a ray tracing procedure, where rays from each voxel of the findings are traced to a position of a camera defined by the camera angle. For each ray, statistics may be calculated to determine a visibility score for the voxel. For example, the statistics may include a distribution of color (e.g., RGB), transparency (RGBA), intensity, and/or other light characteristics along the ray, as the ray passes through various segmented regions of the image volume.

Once the visibility scores have been calculated for each voxel, at 468, calculating the camera angle rendering parameter includes determining a visibility score of the camera angle based on the combined visibility scores of each voxel. In various embodiments, the visibility score of the camera angle may be based on a weighted average of the visibility scores calculated for each voxel of the findings, where each voxel may be weighted by a relative severity of the findings to which the voxel belongs. The relative severity may be determined by the AI algorithm and converted to a scale of 1 to 10, as described above. In other embodiments, the visibility score of the camera angle may be based on a weighted sum of the visibility scores calculated for each voxel of the findings, or a different formula may be used.

For example, the segmented image volume may include a malignant nodule on a lung (e.g., a first finding), and a calcium deposit on a heart (e.g., a second finding) with a low Agatston score, indicating a low risk of heart disease. The ray tracing procedure may determine, for a given camera angle, a first set of visibility scores for a respective first set of voxels of the nodule. The first set of visibility scores may be multiplied by a first, higher weight, where the first weight is based on the malignancy of the nodule. The ray tracing procedure may determine, for the same camera angle, a second set of visibility scores for a respective second set of voxels of the calcium deposit. The second set of visibility scores may be multiplied by a second, lower weight, where the second weight is lower due to the low relative risk of heart disease. The first set of visibility scores and the second set of visibility scores may then be averaged, to determine a weighted average visibility score for the camera angle. In this way, the weighted average visibility score may factor in a higher relative importance of visualizing the nodule than visualizing the calcium deposit.

At 470, calculating the camera angle rendering parameter includes setting rendering parameters for a selected combination of camera FOV and camera angle, where the selected combination of camera FOV and camera angle is the camera angle of the plurality of camera angles that has the highest visibility score. By selecting the combination of camera FOV and camera angle with the highest visibility score, an optimal view of the findings may be determined, where the optimal view shows all the findings most clearly, and where more severe findings may be shown more clearly than less severe findings.

Thus, method 450 provides a procedure for determining an ideal set of rendering parameters for rendering different anatomies of a subject in light of one or more pathologies detected by one or more AI algorithms. By applying method 450, an amount of computation used for rendering the different anatomies may be reduced, with respect to conventional rendering methods, as a result of selectively rendering regions of interest to highlight the regions of interest, and selectively rendering regions not of interest in a manner that reduces a total amount of imaging data to display (e.g., through use of mesh, transparency, etc.), while still communicating information relevant to the one or more pathologies.

In other embodiments, as an alternative to method 450, one or more, or all of the rendering models described herein may be combined into a single rendering model that that may take as input the image volume and the clinical information about the findings, and may output rendering parameters for rendering various aspects of the select regions and findings. For example, in some embodiments, a single rendering model may output rendering parameters for rendering the color, transparency, texture, camera angle, etc., of the findings and regions.

Some of such embodiments may rely on performing a global grid search on most or all of the desired rendering parameters (e.g., color, transparency, texture, camera angle, etc.). The global grid search may iteratively calculate individual visibility scores of each combination of parameters. A combination of rendering parameters with a highest visibility score may then be selected, and the image volume may be rendered in accordance with the selected combination of rendering parameters. For example, a method for performing the global grid search may be described with the following pseudo code:

```
Set visualisation_score = 0                                        (2)
Set rendering parameters = None
For each color in color_list:
  for each surface texture in surfaces_list:
    for each transparency in transparency_list:
      for each angle in camera_list:
        global_score = 0
          rays = compute ray_tracing (colors, surfaces, transparencies,
          angle)
        for each ray in rays:
              score = analyse_and_compute_score_for_ray(ray)
              add score to global_score
        if global_score > Visualisation_score:
            Visualisation_score = global_score (in the meaning of
            become)
            Set rendering parameters = [color, surface, transparency,
            angle]
```

where color_list is a total set of colors for any region/findings to be rendered, surfaces_list is a total set of textures to be applied to any region/findings to be rendered, transparencies_list is a total set of transparency options (e.g., percentages) for any region/findings to be rendered, and camera_list includes all potential camera angles, based on defined increments (e.g., every 5°, or another suitable angle increment) and any pre-defined constraints. For example, in some scenarios, the camera angle may be constrained to a range of angles that are within a threshold proximity of an original coronal view. Constraints may also be defined for other parameters, for example, a color (e.g., red) may be reserved for indicating a severity of a pathology, etc.

In other embodiments, a single rendering model may be implemented as a deep learning (DL) convolutional neural network (CNN) that may be trained on historical rendering parameter data to output a combination of rendering parameters. One advantage of using a single rendering model method rather than method 450 is that interactions and dependencies between rendering the various aspects of the select regions and findings may be addressed more efficiently. For example, the single rendering model may output rendering parameters for color, transparency, and texture that are more complementary in a final visualization than rendering parameters generated using method 450. However, a disadvantage of performing the global grid search or training a DL CNN is that an amount of computation and a time used to generate the rendering parameters may be higher than using method 450. Additionally, advantages of the exhaustive global grid search may be achieved to a degree by performing method 450 a plurality of times, for example, where steps 454-462 are performed in different orders, to generate a plurality of suitable combinations of rendering parameters. An ideal combination of rendering parameters may then be selected from the plurality of suitable combinations based on relative visibility scores of each of the plurality of suitable combinations. Alternatively, the plurality of suitable combinations may be provided as options to a viewer, and the viewer may select a preferred combination of rendering parameters, or alternate between different combinations of rendering parameters.

Further, in some examples, the one or more rendering models may be applied individually to a plurality of pathologies included in the findings, to generate ideal rendering parameters for each finding of a set of findings. For example, the findings may include a first pathology, and a second pathology. A first procedure (e.g., method 450, the global grid search, etc.) may be performed to determine a first set of rendering parameters with which to display the first pathology. A second procedure, which may the same as or different from the first procedure, may be performed to determine a second set of rendering parameters with which to display the second pathology. The first and second sets of rendering parameters may be provided as options to a viewer, and the viewer may select either the first or second sets of rendering parameters to display the image volume, or the viewer may alternate between the first or second sets of rendering parameters.

FIGS. 5-15 shows examples of enhanced visualizations of findings in an image volume, where the findings are generated by one or more AI algorithms, in contrast with exemplary conventional (e.g., prior art) visualizations of the findings generated by a software application for displaying the image volume. For example, the software application may be a medical exam review application launched on a computer or workstation of a caregiver or radiologist. The enhanced visualizations may be generated by an image processing system, such as image processing system 302, by following one or more steps of methods 400 and 450.

Figure 5:
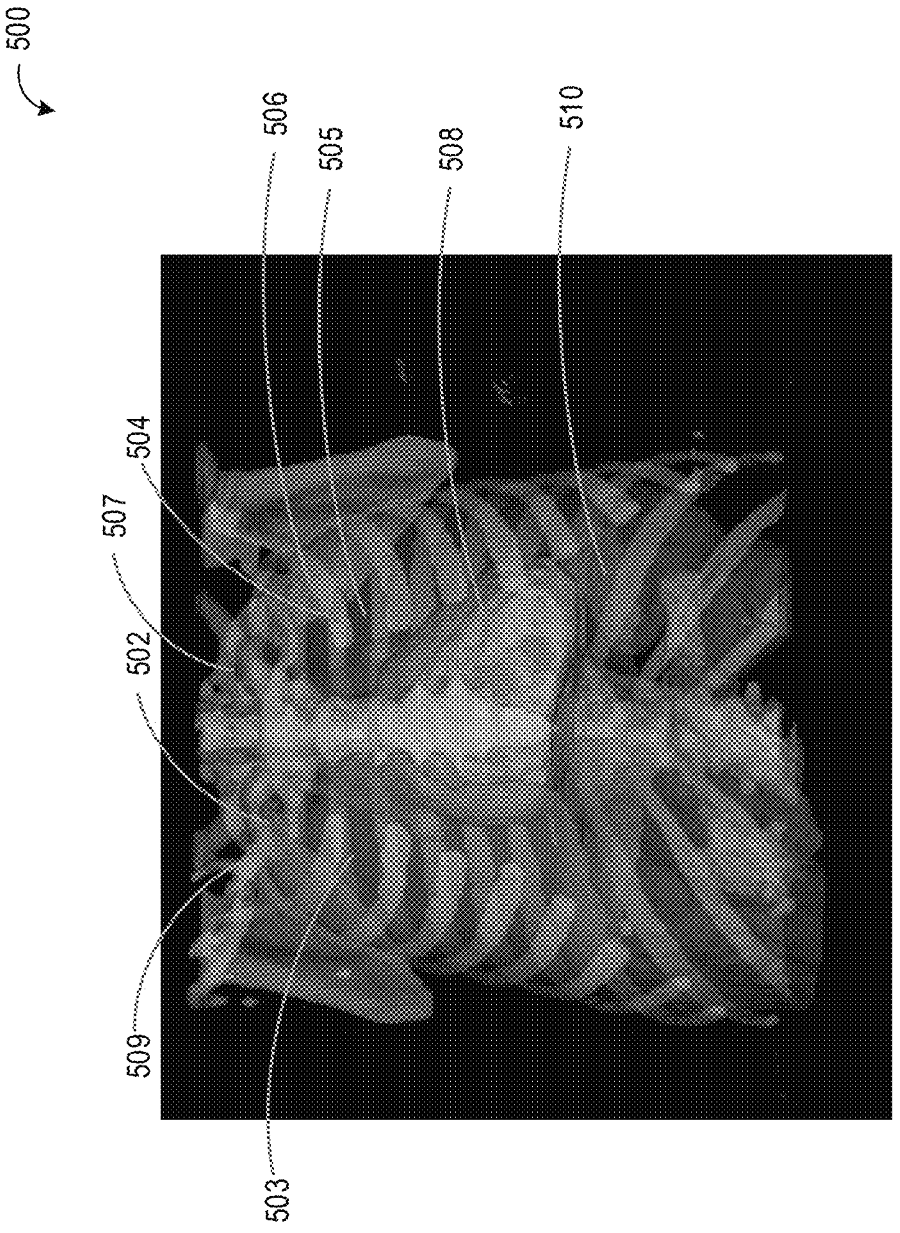
FIG. 5 (Prior Art)
FIG. 5 is an image showing a conventional visualization of nodules on lungs of a patient, as prior art.

Turning first to FIG. 5, a conventional visualization 500 of nodules detected on lungs of a patient is shown, where conventional visualization 500 may be generated by a software application for viewing the image volume. For example, the software application may be coupled to or integrated into an imaging system, such as the X-ray imaging systems 100 and 200 of FIGS. 1 and 2, or the software application may be a medical exam review application used by a caregiver or radiologist to review medical images of patients, such as medical exam review application 338 of FIG. 3. Conventional visualization 500 shows a first nodule 502 on a first lung 503, and a second nodule 504 on a second lung 505, which may be detected and identified by one or more AI algorithms. First nodule 502 and second nodule 504 are rendered in a bright red color, which allows first nodule 502 and second nodule 504 to be distinguished from lungs 503 and 505, which are rendered in a gray color with a high degree of transparency. First nodule 502 and second nodule 504 are also distinguished from a skeleton 507 of the patient, which is rendered in a tan color. Other organs are visible in conventional visualization 500, such as a heart 508, which is rendered in a solid yellow/orange color, and a liver 510, which is rendered in a translucent violet color.

However, the depiction of first nodule 502 and second nodule 504 in conventional visualization 500 may not be ideal. In particular, first nodule 502 lies behind a first rib 509 of skeleton 507, and second nodule 504 lies behind a second rib 506 of skeleton 507. Although the transparency with which skeleton 507 is rendered allows nodules 502 and 504 to be seen, details of nodules 502 and 504 may be partially or totally obscured by ribs 509 and 506. Additionally, the degree of transparency of lungs 503 and 505 is too high to communicate any information about how first nodule 502 is positioned on first lung 503, or how first nodule 502 impacts first lung 503, and how second nodule 504 is positioned on second lung 505, or how second nodule 504 impacts second lung 505. Heart 508 is unaffected by second nodule 504, but it obscures second lung 505, which may be affected by second nodule 504. In fact, a third nodule on second lung 505 may be obscured by heart 508, which the viewer would not see. Liver 510 is shown, but does not contribute any valuable information with respect to the pathologies of first nodule 502 and second nodule 504.

Figure 6:
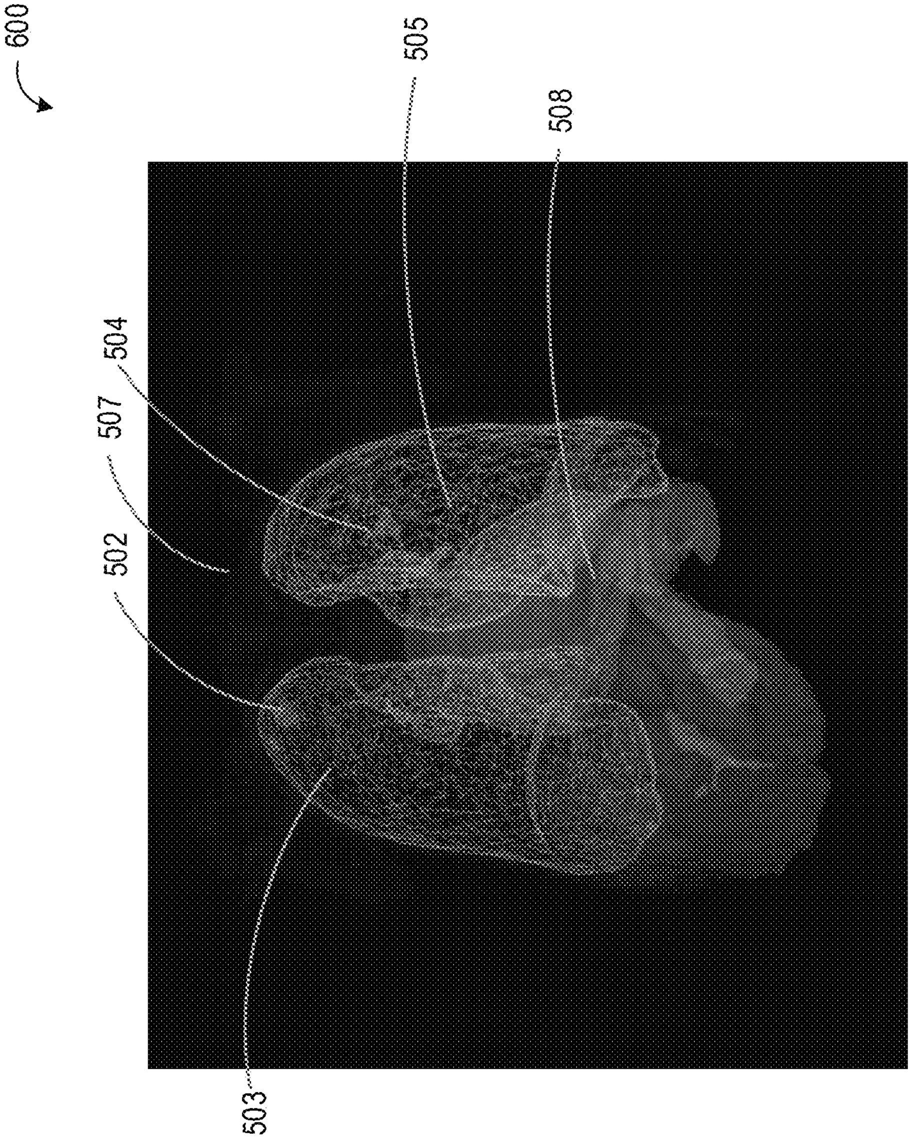
FIG. 6 is a first enhanced visualization of the nodules of FIG. 5, in accordance with one or more embodiments of the present disclosure.

FIG. 6 shows a first enhanced visualization 600 of first nodule 502 and second nodule 504. Similar to FIG. 5, nodules 502 and 504 are rendered in the bright red color. The bright red color may indicate that nodules 502 and 504 are malignant. If nodules 502 and 504 are benign, a different color may be used, such as yellow. In contrast to FIG. 5, in first enhanced visualization 600, skeleton 507 has been rendered in a blue color with a high degree of transparency, such that skeleton 507 is only faintly seen. As such, nodules 502 and 504 are no longer obscured by ribs 509 and 506, respectively, which are not visible. The rendering of skeleton 507 may be achieved using color and transparency rendering models of the image processing system, such as transparency model 312 and organ color model 316 of FIG. 3, for example. Additionally, lungs 503 and 505 are depicted with a mesh texture rather than a color, which more clearly shows surfaces of first lung 503 and second lung 505, while remaining transparent enough for nodules 502 and 504 to be seen. In some examples, the mesh may be used to indicate that lungs 503 and 505 are organs that are impacted by nodules 502 and 504. Pulmonary nodules may not directly impact an appearance of first lung 503 and second lung 505, but it may be important to visualize where the nodule 503 and 505 are inside first lung 503 and second lung 505, and especially in which lobes the nodules are. For example, a precise location (e.g., intraparenchymal, juxtapelural, etc.) of nodules 502 and 504, a closeness of nodules 502 and 504 to the airways or to lung vessels, a type of the nodules 502 and 504 (e.g., solid, part-solid, ground glass), and/or other characteristics may be relied on to classify a severity of the nodules 502 and 504, and/or to perform a biopsy or a lobectomy (or other treatments).

The mesh texture may be generated by a texture rendering model, such as texture model 318. Heart 508 is rendered behind the mesh surfaces of lungs 503 and 505, such that it no longer obscures part of second lung 505. Additionally, a coronal camera angle is selected by the image processing system as optimal for visualizing nodules 502 and 504. As a result, a viewer of first enhanced visualization 600 may more clearly discern a location, positioning, size, and other characteristics of nodules 502 and 504 than in conventional visualization 500.

Figure 7:
FIG. 7 is a second enhanced visualization of the nodules of FIG. 5, in accordance with one or more embodiments of the present disclosure.

FIG. 7 shows a second enhanced visualization 700 of first nodule 502 and second nodule 504. Second enhanced visualization 700 includes a similar rendering of nodules 502 and 504, heart 508, skeleton 507, and the mesh surface texture of lungs 503 and 505. In addition, lungs 503 and 505 have been colorized (e.g., by the color rendering model) in an orange color, to indicate that lungs 503 and 505 are organs that are affected by nodules 502 and 504, in contrast with heart 508, which is rendered in a green color, indicating that heart 508 is not affected by nodules 502 and 504. In this way, the image processing system renders the findings of the AI algorithms (nodules 502 and 504) and anatomical regions/organs/systems that are affected or unaffected by the findings in a manner that not only allows the viewer to more precisely view visual characteristics of nodules 502 and 504, but also conveys additional information about the severity of nodules 502 and 504 and the degree to which other organs are affected.

Figure 8:
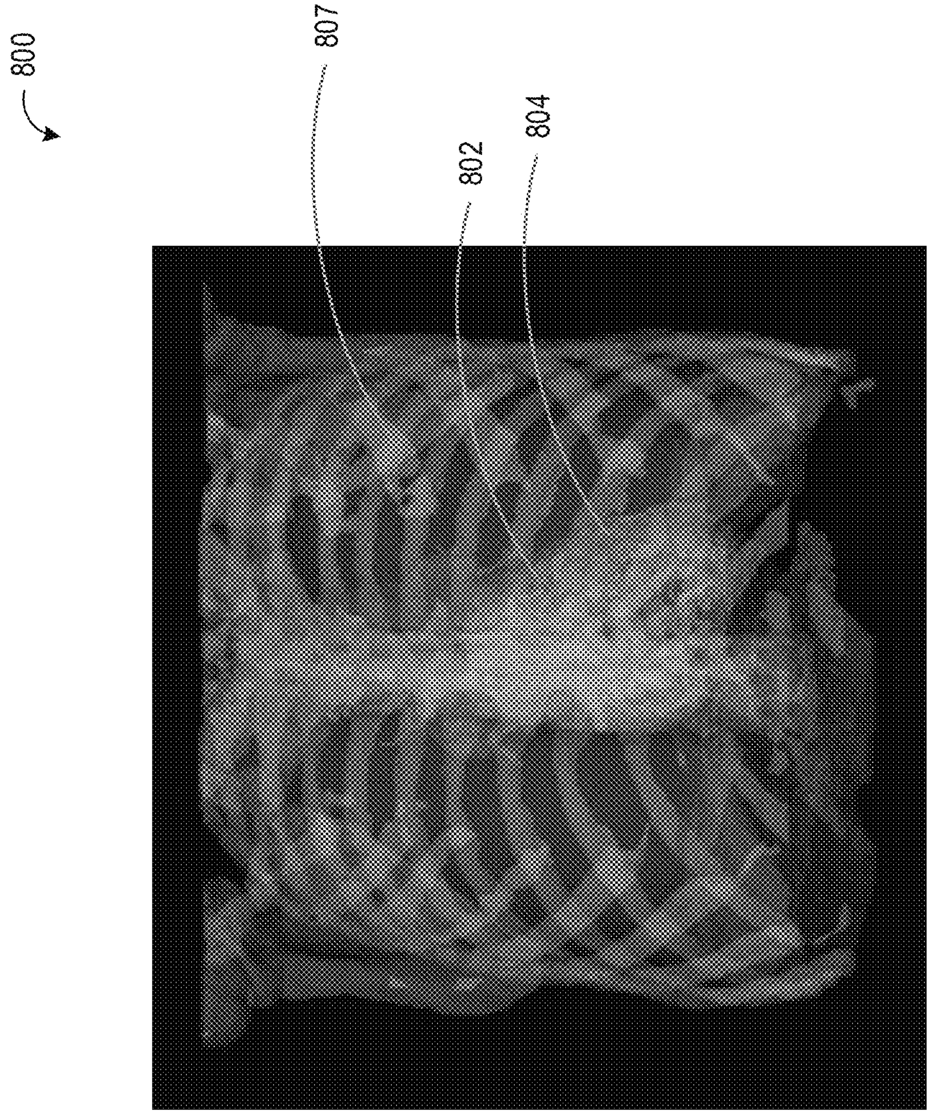
FIG. 8 (Prior Art)
FIG. 8 is an image showing a conventional visualization of calcium scoring on a liver of a patient, as prior art.

Similar to FIG. 5, FIG. 8 shows a conventional visualization 800 of a set of calcium deposits 802 detected on a heart 804 of a patient, where conventional visualization 800 may be generated by the software application for viewing the image volume. The set of calcium deposits 802 may be detected and scored by one or more AI algorithms, as with nodules 502 and 504 of FIGS. 5-7. The set of calcium deposits 802 is rendered in a bright red color, which allows the set of calcium deposits 802 to be distinguished from heart 804, which is rendered in a solid yellow color. However, a skeleton 807 of the patient, is rendered in a tan color, such that portions of heart 804 may be obscured, clouded by, or not distinguishable from portions of skeleton 807.

Figure 9:
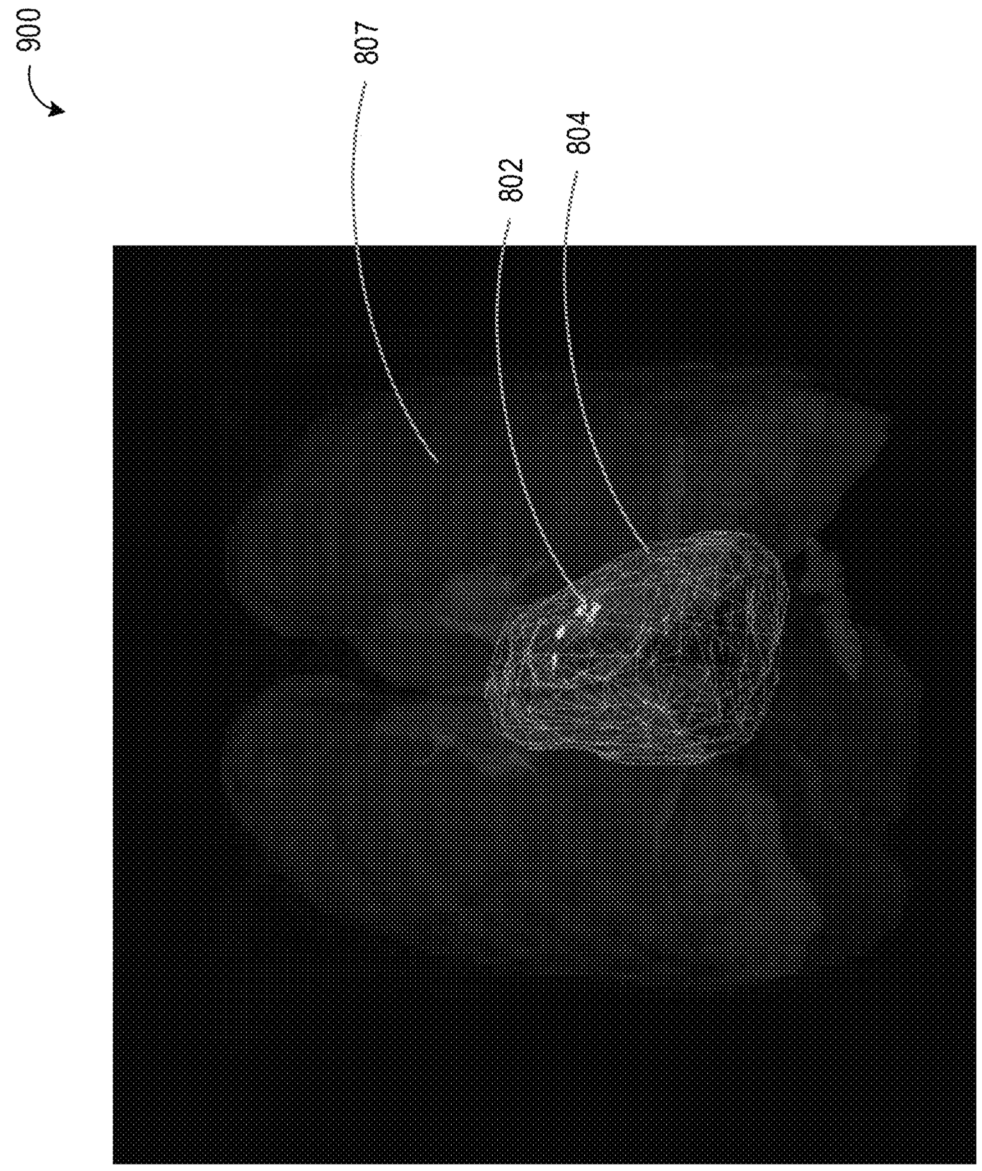
FIG. 9 is a first enhanced visualization of the calcium scoring of FIG. 8, in accordance with one or more embodiments of the present disclosure.

In contrast, FIG. 9 shows a first enhanced visualization 900 of the set of calcium deposits 802, where heart 804 is rendered with a blue mesh texture, similar to lungs 503 and 505 of FIGS. 5-7. The set of calcium deposits 802 may be scored by a relevant AI algorithm prior to rendering. The score, also referred to as an Agatston score, corresponding to an amount of calcium within coronary arteries of heart 804. It is directly correlated to a risk of heart attacks. Calcified plaques in the coronary arteries can narrow the arteries, which can lead to heart diseases (heart attack, strokes). Specifically, the calcium score is a number describing a quantity of calcium deposits in the coronary arteries. Any score above zero could indicate evidence of coronary artery disease, and a higher calcium score could indicate risk of heart attack. Thus, the blue mesh texture may be generated by the texture model to indicate that heart 804 is an organ that is affected by the set of calcium deposits 802 (e.g., heart 804 is at risk due to the presence of a calcium deposit having a higher calcium score). Skeleton 807 is rendered with a high degree of transparency, such that skeleton 807 is barely visible. As a result, the set of calcium deposits 802 is more clearly visible on heart 804 than in conventional visualization 800. The set of calcium deposits 802 is rendered in the bright red color, which may indicate an amount of calcium. For example, the color rendering model may render the color based on a yellow-red gradient, depending on the amount of calcium, where higher amounts of calcium may cause the set of calcium deposits 802 to be rendered in a more red color, and lower amounts of calcium may cause the set of calcium deposits 802 to be rendered in a less red color. Other organs in the image volume that are not affected by calcium scoring may be rendered with high transparency, to reduce a visibility of the other organs.

Figure 10:
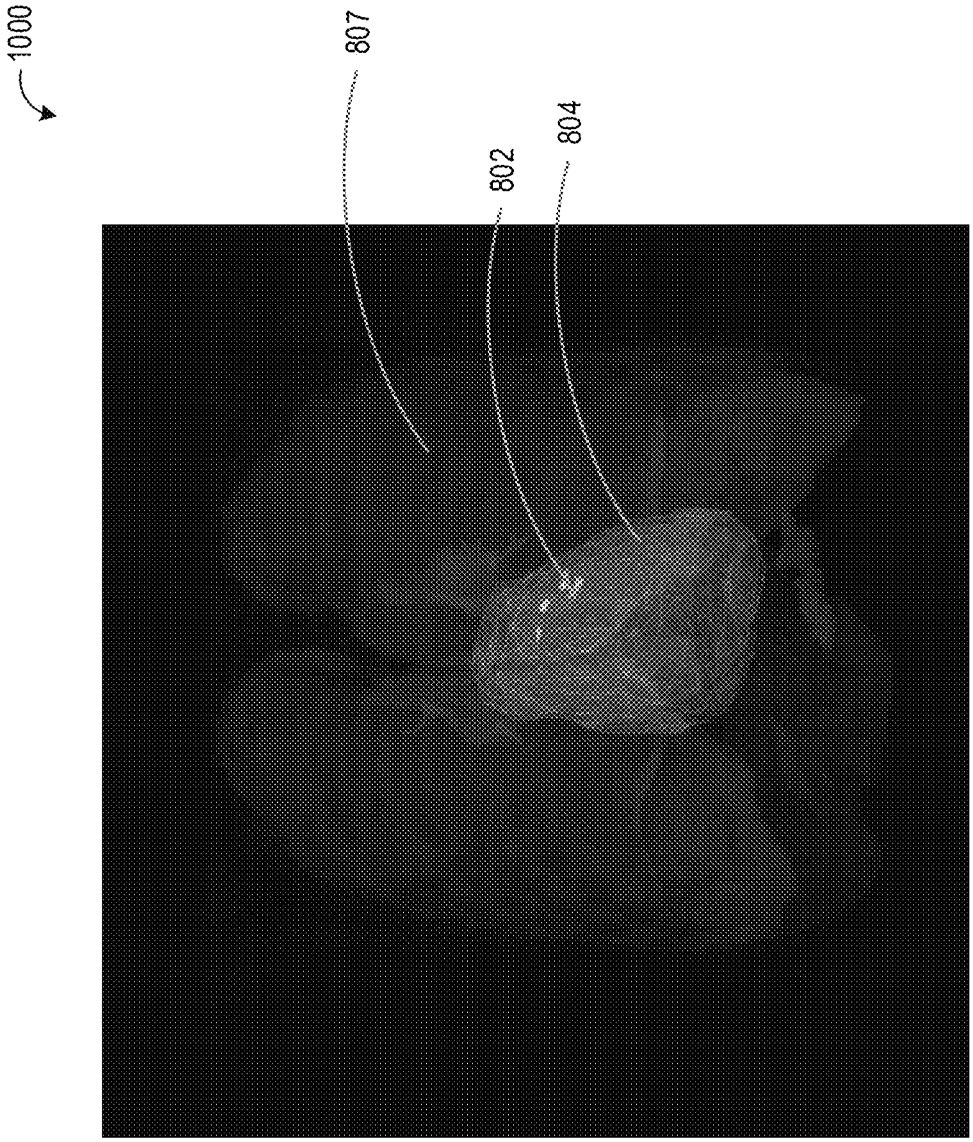
FIG. 10 is a second enhanced visualization of the calcium scoring of FIG. 8, in accordance with one or more embodiments of the present disclosure.

FIG. 10 shows a second enhanced visualization 1000 of the set of calcium deposits 802, where heart 804 is rendered with a red-violet color, similar to lungs 503 and 505 of FIGS. 5-7. The red-violet color may indicate that heart 804 is at risk due to the set of calcium deposits 802, based on a calcium scoring of the set of calcium deposits 802. As with first enhanced visualization 900, other organs, such as lungs, liver, etc., that are not affected by the set of calcium deposits 802 are rendered with high transparency (e.g., by the transparency model), such that they are barely visible. As such, the other organs do not constitute a distraction to the viewer, who may focus full attention on the calcium scoring of the set of calcium deposits 802 and heart 804. In this way, the image processing system advantageously renders the findings and affected regions of the AI algorithms to maximally convey information about pathologies and affected organs and systems, while diminishing a visibility of other portions of an anatomy of the patient that are unaffected and/or may obscure or distract the viewer from the more important findings.

Figure 11:
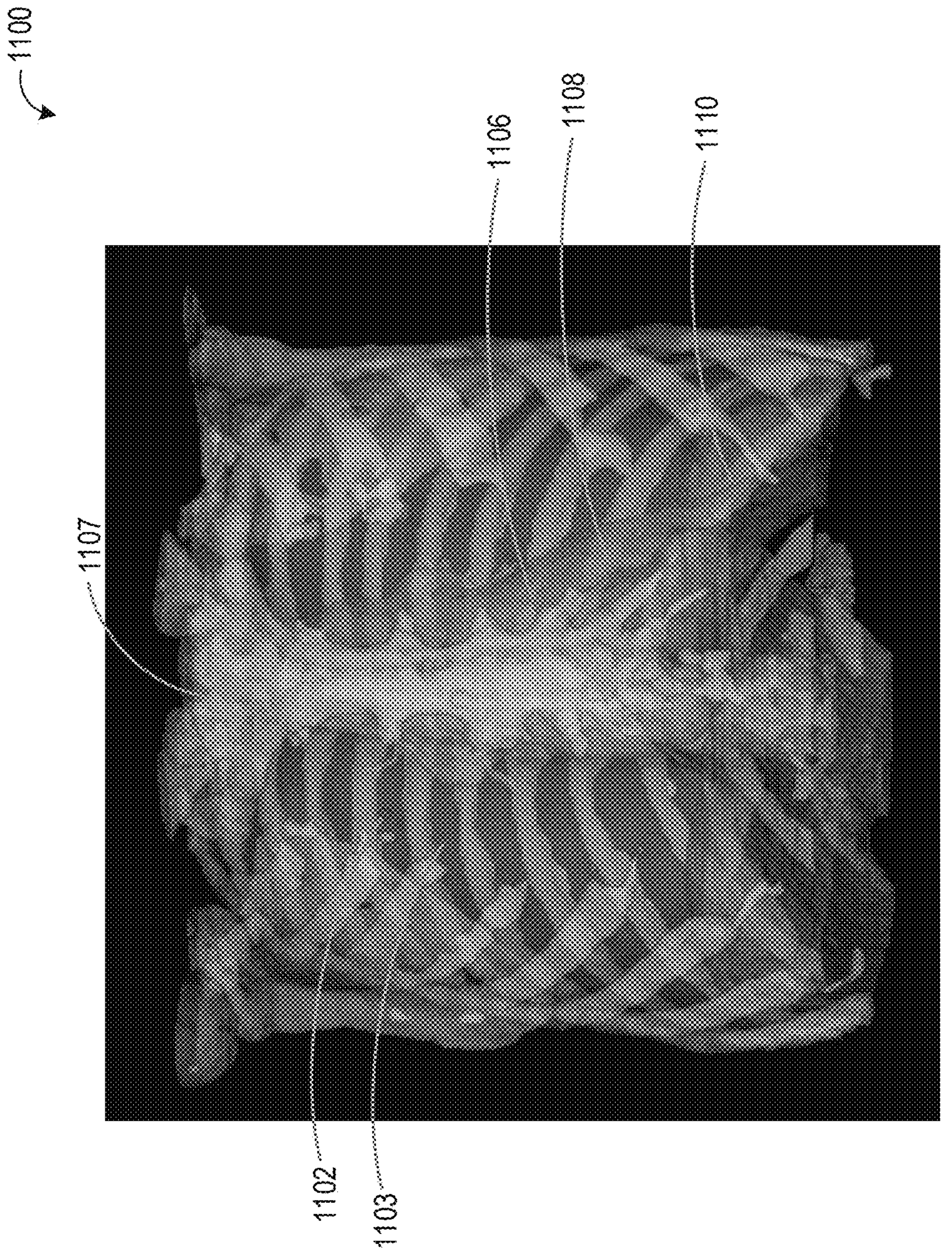
FIG. 11 (Prior Art)
FIG. 11 is an image showing a conventional visualization of both of the nodules and the calcium scoring together, as prior art.

FIG. 11 shows an example of a conventional visualization 1100 of an image volume including both a nodule 1102 on a lung 1103 of a patient and a set of calcium deposits 1106 detected on a heart 1108 of a patient, where conventional visualization 1100 may be generated by the software application for viewing the image volume. As in FIGS. 5-10, nodule 1102 and the set of calcium deposits 1106 are rendered in a bright red color. However, a skeleton 1107 of the patient is rendered in a tan color and with low transparency, such that skeleton 1107 obscures and clouds details of portions of the set of calcium deposits 1106. Additionally, conventional visualization 1100 includes a heart 1108 that is rendered in a similar, tan color, whereby heart 1108 is both obscured by portions of skeleton 1107 and difficult to distinguish from portions of skeleton 1107. With this color and transparency scheme, heart 1108 is only vaguely visible, and details regarding a shape, contour, and surface of heart 1108 cannot be clearly seen. Conventional visualization 1100 includes a representation of a liver 1110, which is similarly difficult to view, although unaffected by either of nodule 1102 and the set of calcium deposits 1106. An impact of nodule 1102 on lung 1103 is not communicated, nor is an impact of the set of calcium deposits 1106 on heart 1108. A severity and extent of the set of calcium deposits 1106 may not be discerned in conventional visualization 1100.

Figure 12:
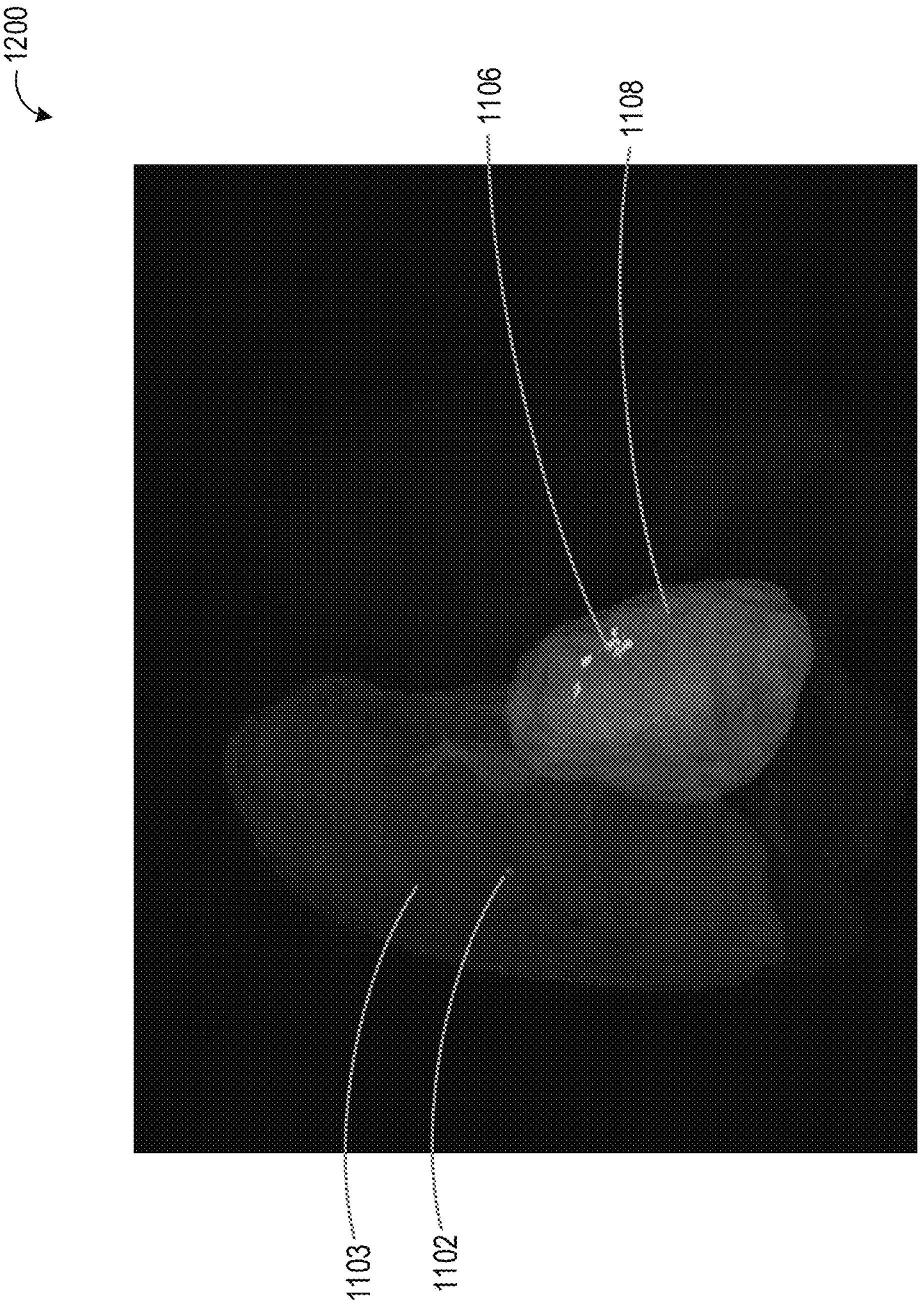
FIG. 12 is a first enhanced visualization of both of the nodules and the calcium scoring together, in accordance with one or more embodiments of the present disclosure.

FIG. 12 shows a first enhanced visualization 1200 of nodule 1102 and the set of calcium deposits 1106, where in contrast to FIG. 11, lung 1103 is rendered with a red color with medium transparency. The red color may communicate to the viewer that lung 1103 is affected by nodule 1102, which is malignant. The medium transparency of lung 1103 allows heart 1108 to be seen behind a portion 1112 of lung 1103, as lung 1103 is positioned in front of heart 1108. Heart 1108 is rendered in a yellow color, indicating that heart 1108 may have a medium risk of heart disease by the set of calcium deposits 1106. As a result of the medium risk, the set of calcium deposits 1106 may warrant a closer examination. Heart 1108 is rendered with low transparency, as the set of calcium deposits 1106 is present on a surface of heart 1108 and is not obscured by any portions of heart 1108. Skeleton 1107 and liver 1110 are rendered with a high degree of transparency, making them invisible. Thus, skeleton 1107 no longer obscures or clouds the view of nodule 1102, lung 1103, the set of calcium deposits 1106, and heart 1108, and a viewer is not distracted by the presence of the unaffected liver 1110. In this way, first enhanced visualization 1200 advantageously focuses the viewer's attention on the findings (nodule 1102 and the set of calcium deposits 1106) and the affected regions (lung 1103 and heart 1108). As a result, the viewer may more clearly see details and characteristics of nodule 1102 and the set of calcium deposits 1106, which may lead to a faster and more accurate diagnosis.

Figure 13:
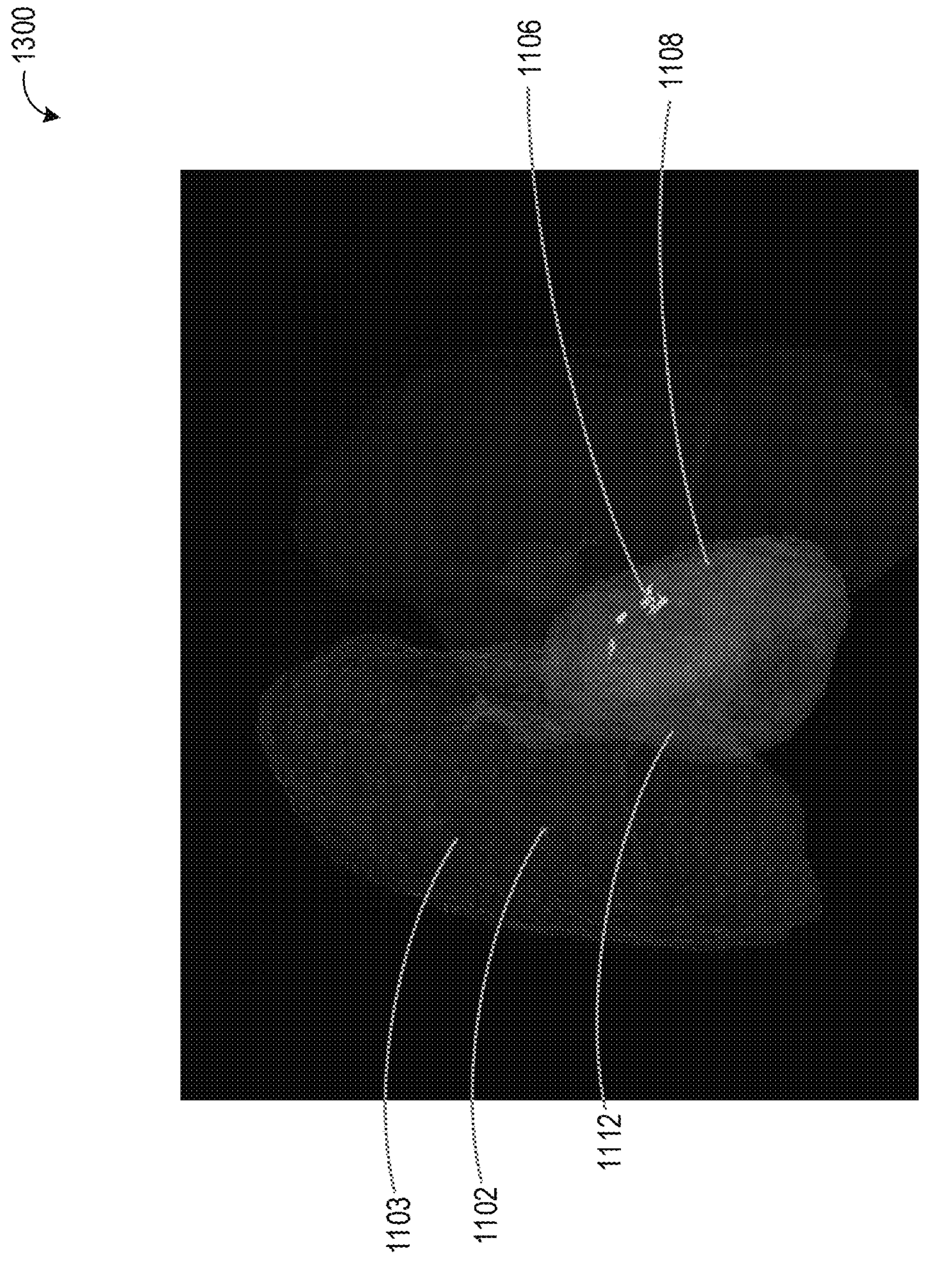
FIG. 13 is a second enhanced visualization of both of the nodules and the calcium scoring together, in accordance with one or more embodiments of the present disclosure.

FIG. 13 shows a second enhanced visualization 1300 of nodule 1102 and the set of calcium deposits 1106, where lung 1103 is rendered with a blue color, which may indicate an alternative scenario where nodule 1102 is benign, and thus a functioning of lung 1103 is severely impacted by nodule 1102. However, heart 1108 is rendered with a magenta color rather than a yellow color. The magenta color may communicate to the viewer that heart 1108 is affected by the set of calcium deposits 1106. As with FIG. 12, skeleton 1107 and liver 1110 are rendered with a high degree of transparency, making them invisible. Alternatively, in some embodiments, the color of lung 1103 may be selected for the purpose of differentiating lung 1103 from the magenta color of heart 1108, and not to communicate an impact of nodule 1102 on lung 1103.

Figure 14:
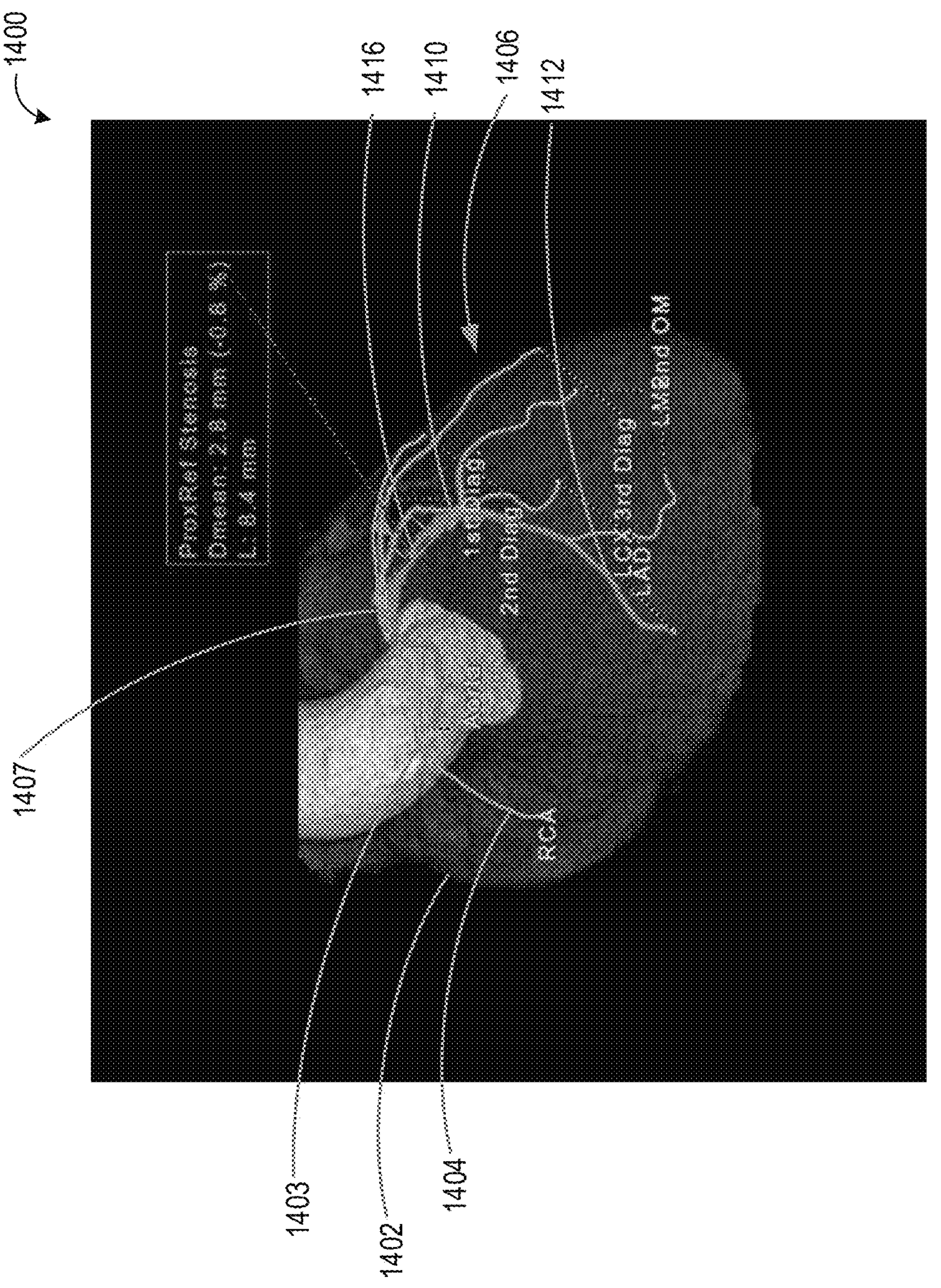
FIG. 14 (Prior Art)
FIG. 14 shows a conventional visualization of a heart of a patient with coronary stenosis, as prior art.

FIG. 14 shows an example of a conventional visualization 1400 of an image volume of a heart 1402, where conventional visualization 1400 may be generated by a software application for viewing the image volume. Conventional visualization 1400 shows a first perspective view of an arrangement of coronary arteries 1406 descending from an aorta 1403 of heart 1402. Coronary arteries 1406 include a right coronary artery 1404 and a left main coronary artery (LMCA) 1407, from which a left circumflex artery (LCX) 1410 and a left anterior descending artery (LAD) 1412 descend. Conventional visualization 1400 further shows a stenosis 1416 in LCX 1410. However, due to a first camera angle of conventional visualization 1400, the first perspective view of conventional visualization 1400 does not position or orient heart 1402 to clearly show stenosis 1416. As a result, characteristics of stenosis 1416 may not be easily viewed.

Figure 15:
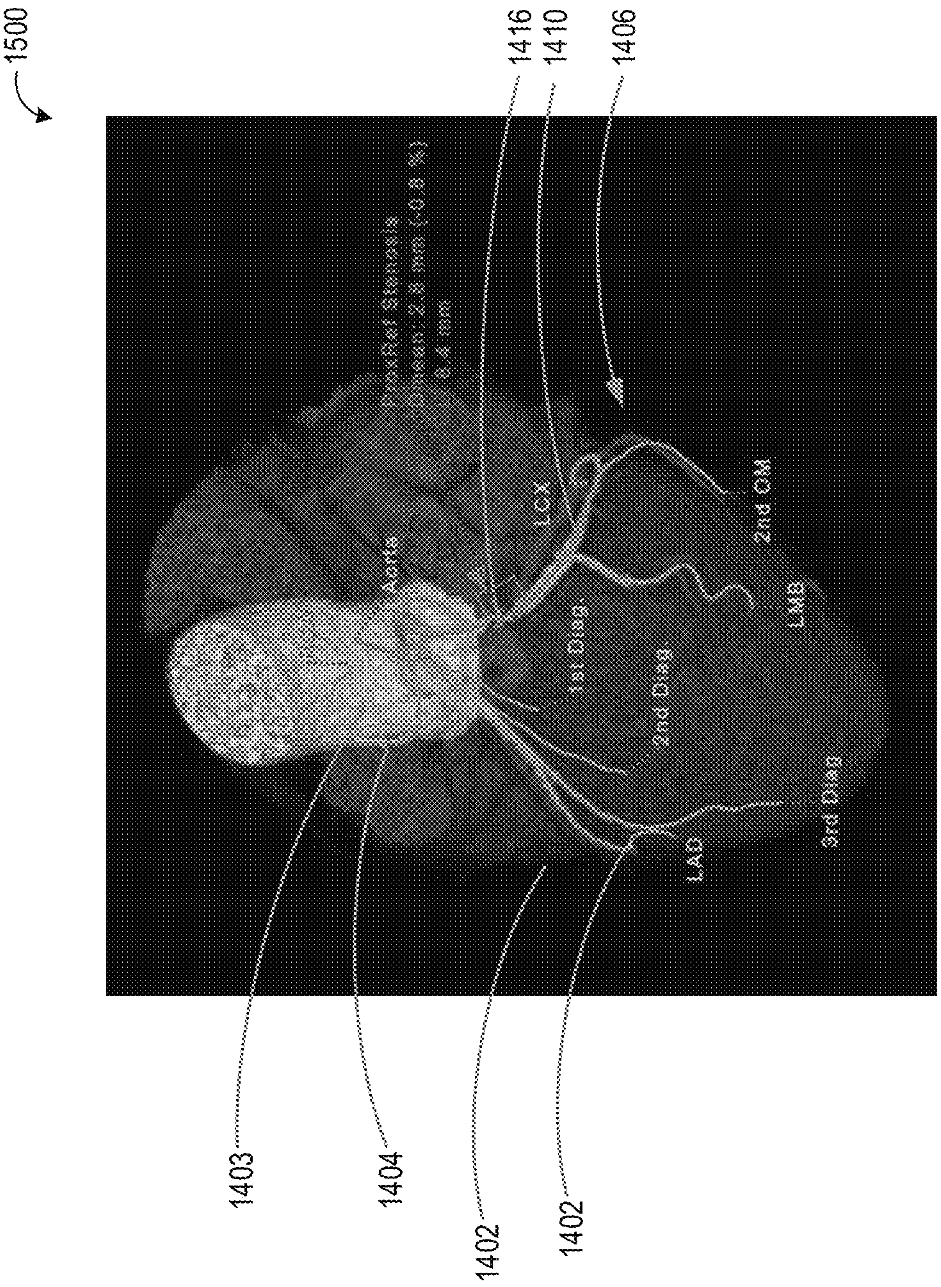
FIG. 15 shows an enhanced visualization of the heart with the coronary stenosis, in accordance with one or more embodiments of the present disclosure.

In contrast, FIG. 15 shows an enhanced visualization 1500, where enhanced visualization 1500 shows a second perspective view of the arrangement of coronary arteries 1406, taken from a second camera angle. The second camera angle may be calculated and/or selected by the image processing system to optimize a visibility of stenosis 1416. In accordance with the second camera angle, heart 1402 is rotated in three dimensions such that stenosis 1416 is centered in the second perspective view. As a result of stenosis 1416 being centered, the arrangement of coronary arteries 1406 appears more spread out than in conventional visualization 1400, where space between the coronary arteries is increased. That is, in contrast to conventional visualization 1400, where coronary arteries 1406 are depicted close together in a smaller area of the image volume, enhanced visualization 1500 shows a clear differentiation between LCX 1410, LAD 1412, and other coronary arteries, which are shown in a larger area. As a result of the increased space between the coronary arteries, a viewer of enhanced visualization 1500 may view details and characteristics of stenosis 1416, such as an exact location of stenosis 1416 and a name of a branch on which the stenosis 1416 appears (e.g., proximal, distal), more rapidly and efficiently than in conventional visualization 1400.

Thus, an image processing system and an automated workflow for generating an enhanced 3D visualization of findings and affected organs of an imaging examination is disclosed, where rendering parameters (camera position, transparency/opacity, color, angle of view, use of mesh) may be optimized to more clearly show the findings and affected organs. The findings may be identified by one or more AI algorithms of the image processing system, the imaging system, or a different system. A camera angle of the enhanced visualization may minimize an overlap between findings and affected organs to show the findings clearly, and a use of transparency, color and mesh may be optimized to ensure that findings are not obscured or clouded, and to communicate additional clinical information about a severity or other characteristics of a pathology of the findings to a viewer.

To highlight zones where findings were found and provide information on the severity of the findings, the severity of findings may be correlated with a level of transparency applied to surrounding organs/regions of the findings. Surrounding organs/regions may be represented and the camera position may be selected to ensure that findings are not hidden or obscured. Additionally or alternatively, a color map based on the severity of the finding may be used. Additionally, the rendering parameters could be adjusted on a voxel-by-voxel basis based on a distance of each voxel to the finding.

The technical effect of generating an enhanced visualization of findings of an imaging exam by generating custom rendering parameters that display the findings and organs and systems surrounding the findings with different colors, textures, transparencies and at a camera angle that optimizes a visibility of the findings, is that a viewer of the enhanced visualization may more rapidly and efficiently examine the findings, resulting in more accurate diagnoses. As a result of the viewer being able to more rapidly and efficiently examine the findings, a use of imaging system and image processing system resources may be reduced, thereby increasing a functioning and an overall efficiency of the imaging system and image processing system. Additionally, a consumption of memory and computing resources used by an imaging system and computational systems used to display an image volume may be decreased as a result of using the customized rendering parameters rather than default or conventionally-determined rendering parameters. The customized rendering of elements may not represent an additional computational process, since anatomical structures and features of a patient are rendered in any case. Rather, by substituting the customized rendering process described herein for a conventional rendering process, an amount of overall computation performed to generate the display may be reduced.

For example, in accordance with the methods described herein, various solid renderings of organs in a conventional display of the image volume may be replaced with mesh renderings that rely on significantly less computation. Alternatively, regions of the image volume that are unaffected by pathologies in the findings may be rendered in a highly transparent fashion, such that the unaffected regions are barely visible, which may be computationally less intensive to render. By showing the findings and affected regions, and not showing the unaffected regions (e.g., bone, organs that obscure the findings), not only is it faster and more efficient for the reviewer to examine the findings, but the display may also be rendered more rapidly and in a less computationally intense manner. As a result, reviewing the findings may be less time-consuming, further reducing the use of computational and memory resources and freeing up the resources for use on other tasks.

Additionally, in some examples, customized rendering parameters may be stored in the image processing system, where the customized rendering parameters may be accessed, selected, and applied by a viewer of the image volume. For example, a set of customized rendering parameters for displaying a first malignant nodule of a lung of a first patient may be appropriate for displaying a second malignant nodule of a lung of a second patient. In this way, sets of customized rendering parameters may be compiled and reused, which may further reduce the amount of computation performed by the image processing system.

Thus, by facilitating an efficient review of the findings, an overall use of the imaging system may be reduced. If details of the findings cannot be clearly seen in the conventional display, additional imaging studies may be performed, increasing a use of the imaging system and decreasing an availability of the imaging system for use with other patients. By using the customized rendering approach described herein, a visibility of the findings may be maximized, allowing reviewers to discern more detailed characteristics of pathologies detected and identified by the AI algorithms.

Further, individual renderings of different organs and systems may be used to convey additional clinical information about the findings, such as a severity of the pathologies, which may not be visually indicated by a conventional visualization that does not use the customized rendering approach described herein. By communicating the additional information, the reviewer may spend less time consulting other medical records of the patient.

The customized rendering approach may rely on various models to determine custom rendering parameters for findings, organs, and systems with respect to different aspects of the display. For example, a first custom rendering model may be applied to adjust a color of the findings, organs, and systems; a second custom rendering model may be applied to adjust a transparency of the findings, organs, and systems; a third custom rendering model may be applied to adjust a texture of the findings, organs, and systems; and so on. By using different models to adjust the different aspects of the display, a flexibility and robustness of the image processing system may be increased. For example, a more detailed, comprehensive, and/or customized model may be easily substituted for a less detailed, comprehensive, and/or customized model, without affecting a performance of other rendering models. Additionally or alternatively, customized rendering parameters may be determined based on a combined output of a plurality of rendering models, to increase a visibility of the findings.

Further, the models may be structured to take a standardized set of inputs, such that inputs into each rendering model are the same. In other words, in accordance with the methods disclosed herein, the outputs of a wide and growing body of AI algorithms for detecting and identifying pathologies may be reformatted into a standardized input format relied on by the rendering models. As a result of the reformatting, additional AI algorithms and additional rendering models may be used and/or incorporated into the image processing system at a marginal cost, and with a more streamlined use of computational resources. The standardized input format may also encourage and/or result in an increased standardization of the outputs of the AI algorithms.

The disclosure also provides support for a method for an image processing system, the method comprising: receiving an image volume of an anatomy of a patient, performing a segmentation of anatomies of the image volume, applying one or more artificial intelligence (AI) algorithms to the segmented image volume to detect a pathology in the anatomy, and prior to rendering the image volume for display: extracting information about the pathology from findings of the one or more AI algorithms, calculating different, customized rendering parameters for the pathology findings, and for each organ and/or system of a plurality of organs and/or systems surrounding the pathology, based on the extracted information, and rendering the image volume on a display device, based on the customized rendering parameters. In a first example of the method, the extracted information includes one or more of: a position of the pathology, a severity of the pathology, a size of the pathology, dimensions of the pathology, a system of a body of the patient affected by the pathology, and an organ of the patient affected by the pathology. In a second example of the method, optionally including the first example, the customized rendering parameters include parameters for rendering one or more of: a transparency/opacity of a respective organ, or system, a first color of the pathology, a second color of a respective organ, or system, a texture of a surface of a respective organ or system, a camera angle from which the image volume is viewed, and a camera field of view of the image volume. In a third example of the method, optionally including one or both of the first and second examples, the first color is selected or calculated to indicate a severity the pathology, and the second color is selected or calculated to indicate whether the respective organ or system is affected by the pathology. In a fourth example of the method, optionally including one or more or each of the first through third examples: the first color is selected from a first color gradient between a first reference color indicating a higher severity of the pathology, and a second reference color indicating a lower severity of the pathology, and the second color is selected from a second color gradient between a third reference color indicating that the respective organ or system is more affected by the pathology, and a fourth reference color indicating that the respective organ or system is less affected by the pathology. In a fifth example of the method, optionally including one or more or each of the first through fourth examples, the method further comprises: rendering the texture of the surface of the respective organ or system as a mesh that allows the pathology to be visible without being obscured or clouded by the respective organ or system, to indicate that the respective organ or system is affected by the pathology. In a sixth example of the method, optionally including one or more or each of the first through fifth examples, the camera angle is calculated to minimize an overlap between the pathology and the organs and systems surrounding the pathology, and calculating the camera angle further comprises determining color, transparency, and texture rendering parameters, performing a grid search over a plurality of camera angles at set increments, and calculating a visibility score for each camera angle of the plurality of camera angles, and selecting a camera angle with a highest visibility score. In a seventh example of the method, optionally including one or more or each of the first through sixth examples, in response to the respective organ or system being unaffected by the pathology, rendering the respective organ or system with a degree of transparency selected to minimize a visibility of the respective organ or system. In a eighth example of the method, optionally including one or more or each of the first through seventh examples, the method further comprises using a plurality of rendering models to calculate the different, customized rendering parameters, the plurality of rendering models including at least one of a first rendering model for determining color rendering parameters, a second rendering model for determining transparency rendering parameters, and a third rendering model for determining texture rendering parameters. In a ninth example of the method, optionally including one or more or each of the first through eighth examples, the method further comprises: reformatting an output of the one or more AI algorithms to a standardized input format of one or more of the first rendering model, the second rendering model, and the third rendering model. In a tenth example of the method, optionally including one or more or each of the first through ninth examples, the method further comprises: using a single rendering model to calculate the different, customized rendering parameters, the single rendering model performing a global grid search on a set of rendering parameters, and iteratively calculating individual visibility scores of each combination of rendering parameters of the set of rendering parameters, wherein the image volume is rendered in accordance with a combination of rendering parameters having a highest visibility score. In a eleventh example of the method, optionally including one or more or each of the first through tenth examples, calculating the different, customized rendering parameters for the pathology findings further comprises calculating a plurality of different combinations of customized rendering parameters, and enabling a selection of one or more combinations of the plurality of different combinations to render the image volume. In a twelfth example of the method, optionally including one or more or each of the first through eleventh examples, a first combination of customized rendering parameters is calculated for viewing a first pathology finding of the pathology findings, and a second combination of customized rendering parameters is calculated for viewing a second pathology finding of the pathology findings.

The disclosure also provides support for an image processing system, comprising: a processor, and a memory including instructions that when executed, cause the processor to: receive an image volume of a patient from a medical imaging system, detect a pathology in the image volume using an artificial intelligence (AI) algorithm, prior to rendering the image volume for display: extract clinical information about the pathology from an output of the AI algorithm, calculate customized rendering parameters for each of the pathology and each organ and/or system of a plurality of organs and/or systems surrounding the pathology, based on the extracted clinical information, and render the image volume on a display device, based on the customized rendering parameters. In a first example of the system, further instructions are stored in the memory that when executed, cause the processor to reformat the output of the AI algorithm to a standardized input format of a plurality of rendering models of the image processing system, each rendering model of the plurality of rendering models used to calculate one or more customized rendering parameters relating to one of: a transparency/opacity of a respective organ or system, a color of the pathology, a color of a respective organ, or system, and a texture of a surface of a respective organ or system. In a second example of the system, optionally including the first example, an output of a rendering model of the plurality of rendering models includes a rendering parameter for rendering an organ or system of the plurality of organs and/or systems with a mesh surface, that allows the pathology to visible through the organ or system. In a third example of the system, optionally including one or both of the first and second examples, the mesh surface indicates that the organ or system is affected by the pathology. In a fourth example of the system, optionally including one or more or each of the first through third examples, the customized rendering parameters include a camera angle for displaying the image volume on the display, the camera angle calculated to minimize an overlap between the pathology and the organs and systems surrounding the pathology.

The disclosure also provides support for a method for visualizing findings of one or more artificial intelligence (AI) algorithms trained to detect a pathology in an image volume of an anatomy of a patient, the method comprising: extracting clinical information about the pathology from the findings, processing the extracted clinical information and the image volume using a customized rendering model, to generate a set of customized rendering parameters for rendering the pathology and a plurality of organs and/or systems surrounding the pathology, and rendering the image volume on a display device, based on the set of customized rendering parameters. In a first example of the method, processing the extracted clinical information and the image volume using the customized rendering model to generate the set of customized rendering parameters further comprises: performing a global grid search on a plurality of customized rendering parameters, calculating individual visibility scores of each combination of customized rendering parameters of the plurality of customized rendering parameters, selecting a combination of customized rendering parameters having a highest visibility score.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method for an image processing system, the method comprising:

receiving an image volume of an anatomy of a patient;

performing a segmentation of the image volume into one or more anatomical regions;

applying one or more artificial intelligence (AI) algorithms to the segmented image volume to detect a pathology in the anatomy; and prior to rendering the image volume for display:

extracting information about the pathology from findings of the one or more AI algorithms;

calculating customized rendering parameters for rendering the image volume on a display device based on the extracted information and one or more anatomical regions including a first anatomical region, the customized rendering parameters including:

a camera angle from which the image volume is to be viewed, wherein the camera angle is calculated to minimize an overlap between the pathology and the first anatomical region, and wherein the camera angle is calculated by performing a grid search over a plurality of camera angles at set increments, calculating a visibility score for each camera angle of the plurality of camera angles, and selecting a camera angle with a highest visibility score, a first set of rendering parameters for the pathology, the first set of rendering parameters including a first color, and a second set of rendering parameters, different than the first set of rendering parameters, for the first anatomical region of the one or more anatomical regions, the second set of rendering parameters including a second color; and rendering the image volume on a display device, based on the customized rendering parameters.

2. The method of claim 1, wherein the extracted information includes one or more of:

a position of the pathology;

a severity of the pathology;

a size of the pathology;

dimensions of the pathology;

an indication of a system of a body of the patient affected by the pathology; and an indication of an organ of the patient affected by the pathology.

3. The method of claim 1, wherein the customized rendering parameters include further parameters for rendering one or more of:

a transparency/opacity of the first anatomical region or a second anatomical region of the one or more anatomical regions;

a texture of a surface of the first anatomical region or the second anatomical region; and a camera field of view of the image volume.

4. The method of claim 3, further comprising rendering the texture of the surface of the first anatomical region as a mesh that allows the pathology to be visible without being obscured or clouded by the first anatomical region, to indicate that the first anatomical region is affected by the pathology.

5. The method of claim 3, wherein:

in response to the second anatomical region being unaffected by the pathology, rendering the second anatomical region with a degree of transparency selected to minimize a visibility of the second anatomical region.

6. The method of claim 3, further comprising using a plurality of rendering models to calculate the customized rendering parameters, the plurality of rendering models including:

a first rendering model for determining color rendering parameters;

a second rendering model for determining transparency rendering parameters; and a third rendering model for determining texture rendering parameters.

7. The method of claim 6, further comprising reformatting an output of the one or more AI algorithms to a standardized input format of one or more of the first rendering model, the second rendering model, and the third rendering model.

8. The method of claim 1, wherein the first color is selected or calculated to indicate a severity the pathology, and the second color is selected or calculated to indicate whether the first anatomical region is affected by the pathology.

9. The method of claim 8, wherein:

the first color is selected from a first color gradient between a first reference color indicating a higher severity of the pathology, and a second reference color indicating a lower severity of the pathology; and the second color is selected from a second color gradient between a third reference color indicating that the first anatomical region is more affected by the pathology, and a fourth reference color indicating that the first anatomical region is less affected by the pathology.

10. The method of claim 1, further comprising using a single rendering model to calculate the customized rendering parameters, the single rendering model performing a global grid search on a set of rendering parameters, and iteratively calculating individual visibility scores of each combination of rendering parameters of the set of rendering parameters;

wherein the image volume is rendered in accordance with a combination of rendering parameters having a highest visibility score.

11. The method of claim 1, wherein calculating the customized rendering parameters further comprises calculating a plurality of different combinations of customized rendering parameters, and enabling a selection of one or more combinations of the plurality of different combinations to render the image volume.

12. The method of claim 11, wherein a first combination of customized rendering parameters is calculated for viewing the pathology, and a second combination of customized rendering parameters is calculated for viewing a second pathology of the anatomy.

13. An image processing system, comprising:

a processor, and a memory including instructions that, when executed, cause the processor to:

receive an image volume of a patient from a medical imaging system;

detect a pathology in the image volume using an artificial intelligence (AI) algorithm; and prior to rendering the image volume for display:

extract clinical information about the pathology from an output of the AI algorithm;

calculate customized rendering parameters for each of the pathology and each of one or more organs and/or systems surrounding the pathology, based on the extracted clinical information, wherein the customized rendering parameters include a first, lower transparency for the pathology, a second, higher transparency for a first organ affected by the pathology, and a surface mesh for the first organ, wherein a single rendering model is used to calculate the customized rendering parameters, the single rendering model performing a global grid search on a set of rendering parameters, and iteratively calculating individual visibility scores of each combination of rendering parameters of the set of rendering parameters; and render the image volume on a display device, based on the customized rendering parameters, wherein the image volume is rendered in accordance with a combination of rendering parameters having a highest visibility score.

14. The image processing system of claim 13, wherein the customized rendering parameters further include a the second transparency or a third transparency for a second organ unaffected by the pathology.

15. The image processing system of claim 14, wherein the customized rendering parameters further include a first color for the pathology, a second color for the first organ, and a third color for the second organ.

16. The image processing system of claim 13, wherein the customized rendering parameters include a camera angle for displaying the image volume on the display, the camera angle calculated to minimize an overlap between the pathology and the one or more organs and/or systems surrounding the pathology.

17. A method for visualizing findings of one or more artificial intelligence (AI) algorithms trained to detect a pathology in an image volume of an anatomy of a patient, the method comprising:

extracting clinical information about the pathology from the findings;

processing the extracted clinical information and the image volume using a customized rendering model, to generate a set of customized rendering parameters for rendering the pathology and one or more organs and/or systems surrounding the pathology, the processing including:

performing a global grid search on each of a plurality of combinations of customized rendering parameters;

calculating individual visibility scores of each combination of customized rendering parameters; and selecting a combination of customized rendering parameters from the plurality of combinations having a highest visibility score as the set of customized rendering parameters; and rendering the image volume on a display device, based on the set of customized rendering parameters.

* * * * *